United States Patent
Hunziker et al.

(10) Patent No.: US 8,722,721 B2
(45) Date of Patent: *May 13, 2014

(54) SEC-HYDROXYCYCLOHEXYL DERIVATIVES

(75) Inventors: Daniel Hunziker, Moehlin (CH); Werner Neidhart, Hagenthal-le-Bas (FR)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/414,753

(22) Filed: Mar. 8, 2012

(65) Prior Publication Data

US 2012/0238613 A1 Sep. 20, 2012

(30) Foreign Application Priority Data

Mar. 16, 2011 (EP) ..................................... 11158386

(51) Int. Cl.
*A61K 31/4015* (2006.01)
*C07D 209/54* (2006.01)

(52) U.S. Cl.
USPC ............................ 514/409; 548/407; 548/408

(58) Field of Classification Search
USPC ................................... 548/407, 408; 514/409
See application file for complete search history.

(56) References Cited

U.S. PATENT DOCUMENTS

| | | | |
|---|---|---|---|
| 7,968,585 B2 * | 6/2011 | Mabry et al. ................... | 514/409 |
| 8,097,634 B2 * | 1/2012 | Ackermann et al. .......... | 514/278 |
| 8,329,904 B2 * | 12/2012 | Ackermann et al. ............ | 546/16 |
| 2010/0292212 A1 | 11/2010 | Ackermann et al. | |

FOREIGN PATENT DOCUMENTS

| | | |
|---|---|---|
| WO | 2007/127763 | 11/2007 |
| WO | 2011/045292 | 4/2011 |
| WO | 2011/143163 | 11/2011 |

OTHER PUBLICATIONS

Ackermann et al (2011): STN International HCAPLUS database, (Columbus, Ohio), Accession No. 2011:497600.*
"International Search Report PCT/EP2012/054307 mailed Apr. 17, 2012".
Buchwald et al., "Journal of the American Chemical Society" 124:7421 ( 2002).

* cited by examiner

*Primary Examiner* — Golam M M Shameem

(57) ABSTRACT

The invention provides novel compounds having the general formula (I)

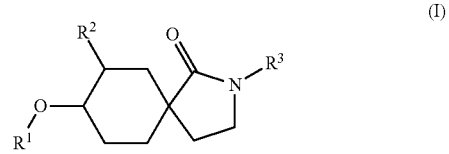

wherein $R^1$, $R^2$ and $R^3$ are as described herein, compositions including the compounds and methods of using the compounds.

24 Claims, No Drawings

SEC-HYDROXYCYCLOHEXYL DERIVATIVES

PRIORITY TO RELATED APPLICATION(S)

This application claims the benefit of European Patent Application No. 11158386.0, filed Mar. 16, 2011, which is hereby incorporated by reference in its entirety.

FIELD OF THE INVENTION

The present invention relates to organic compounds useful for therapy or prophylaxis in a mammal, and in particular to inhibitors of hormone sensitive lipase (HSL) for the treatment of diabetes, metabolic syndrome, dyslipidemia, atherosclerosis, obesity, cardiovascular diseases, myocardial dysfunction, inflammation, nonalkoholic fatty liver disease or nonalkoholic steatohepatitis.

BACKGROUND OF THE INVENTION

The main physiological role of white adipose tissue (WAT) is to supply energy when it is needed by other tissues. In mammals, white adipose tissue is the primary energy storage depot, accumulating fuel reserves in the form of triacylglycerol (TAG) during times of energy excess. The release of free fatty acids (FFA) from TAG is stimulated by catecholamines and regulated by hormones such as insulin, glucagon and epinephrine. The most important enzyme in WAT believed responsible for hormone regulated hydrolysis of triglyceride is hormone sensitive lipase (HSL).

Dysregulation of adipocyte lipolysis, resulting in elevated circulating non-esterified fatty acids (NEFA) is associated with obesity and co-morbidities including the development of type 2 diabetes. Obese or insulin resistant subjects have increased visceral adipose tissue depots. These depots contain elevated levels of HSL protein and exhibit enhanced lipolytic activity as they are resistant to the insulin-mediated suppression of lipolysis. This results in increased plasma levels of free fatty acids (FFA), which further exacerbates insulin resistance due to the accumulation of triglycerides in tissues other than WAT such as liver, pancreas and muscle. Thus, the elevated plasma levels of FFA due to increased HSL activity contributes to and worsens insulin resistance in obese and type 2 diabetic individuals. Restoring the exaggerated plasma FFA and triglyceride levels through inhibition of HSL would reduce the accumulation of triglycerides in tissues other than WAT, such as liver, muscle and the pancreas resulting in decreased hepatic glucose output, increased muscle fatty acid oxidation and improving β-cell function.

Elevated FFAs are also associated with increased cardiovascular risk, including atherosclerosis and myocardial dysfunction. Furthermore, high lipolytic activity and elevated FFAs lead to increased insulin resistance and hypertension in hypertensive rats. The FFA collect in the liver and lead to increased production of TAG, which are packaged into very low density lipoproteins (VLDL) which are secreted. Therefore, reducing the activity of HSL would decrease the release of FFA to the blood, thus limiting the supply of FFA to the liver for TAG synthesis. Thus, HSL inhibitors could have beneficial effects as treatment of nonalkoholic fatty liver disease (NAFLD) and nonalkoholic steatohepatitis (NASH).

SUMMARY OF THE INVENTION

The present invention relates to compounds according to formula (I),

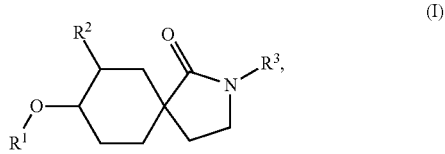

wherein
$R^1$ is selected from the group consisting of hydrogen, alkyl and cycloalkyl;
$R^2$ is selected from the group consisting of hydrogen, alkyl, cycloalkyl, cycloalkylalkyl, alkylcycloalkyl, alkylcycloalkylalkyl, alkoxy, alkoxyalkyl, cycloalkoxy, cycloalkoxyalkyl, haloalkyl, haloalkoxy, haloalkoxyalkyl, halocycloalkyl, halocycloalkylalkyl, halocycloalkoxy and halocycloalkoxyalkyl; and
$R^3$ is selected from the group consisting of phenyl, pyridinyl, pyrazinyl, pyrimidyl and pyridazinyl,
wherein said phenyl, pyridinyl, pyrazinyl, pyrimidyl and pyridazinyl are optionally substituted with one to three substituents independently selected from the group consisting of alkyl, cycloalkyl, cycloalkylalkyl, halogen, haloalkyl, hydroxy, hydroxyalkyl, alkoxy, alkoxyalkyl, haloalkoxy, hydroxyhaloalkyl, alkoxyhaloalkyl and benzyloxyhaloalkyl.

In addition to compounds of formula (I), the present invention also relates to salts and esters of such compounds, the use of such compounds as therapeutically active substances, a process for the manufacture of the said compounds, intermediates, pharmaceutical compositions, medicaments containing the said compounds, their pharmaceutically acceptable salts or esters, the use of the said compounds, salts or esters for the treatment or prophylaxis of illnesses, especially in the treatment or prophylaxis of diabetes, metabolic syndrome, dyslipidemia, atherosclerosis, obesity, cardiovascular diseases, myocardial dysfunction, inflammation, nonalkoholic fatty liver disease or nonalkoholic steatohepatitis and the use of the said compounds, salts or esters for the production of medicaments for the treatment or prophylaxis of diabetes, metabolic syndrome, dyslipidemia, atherosclerosis, obesity, cardiovascular diseases, myocardial dysfunction, inflammation, nonalkoholic fatty liver disease or nonalkoholic steatohepatitis.

DETAILED DESCRIPTION OF THE INVENTION

The term "alkoxy" denotes a group of the formula —O—R', wherein R' is an alkyl group. Examples of alkoxy group include methoxy, ethoxy, n-propoxy, isopropoxy, n-butoxy, isobutoxy and tert-butoxy. Particular alkoxy group include methoxy, ethoxy, n-propoxy and isopropoxy.

The term "alkoxyalkyl" denotes an alkyl group wherein at least one of the hydrogen atoms of the alkyl group has been replaced by an alkoxy group. Exemplary alkoxyalkyl groups include methoxymethyl, ethoxymethyl, methoxymethyl, ethoxyethyl, methoxypropyl and ethoxypropyl. Particular alkoxyalkyl group include methoxymethyl and methoxyethyl.

The term "alkoxyhaloalkyl" denotes an alkyl wherein at least one of the hydrogen atoms of the alkyl has been replaced by an alkoxy group and wherein at least one of the hydrogen atoms of the alkyl has been replaced by a halogen. Examples of alkoxyhaloalkyl include methoxytrifluoroethyl or methoxytrifluoropropyl. Particular alkoxyhaloalkyl is 2,2,2-trifluoro-1-methoxyethyl.

The term "alkyl" denotes a monovalent linear or branched saturated hydrocarbon group of 1 to 12 carbon atoms, in particular of 1 to 7 carbon atoms, more particular of 1 to 4 carbon atoms, for example, methyl, ethyl, n-propyl, isopropyl, n-butyl, iso-butyl, sec-butyl, and tert-butyl. Particular alkyl groups include methyl, ethyl, n-propyl and isopropyl. More particular alkyl group is isopropyl.

The term "alkylcycloalkyl" denotes a cycloalkyl group wherein at least one of the hydrogen atoms of the cycloalkyl group is replaced by an alkyl group. Examples of alkylcycloalkyl include methyl-cyclopropyl, dimethyl-cyclopropyl, methyl-cyclobutyl, dimethyl-cyclobutyl, methyl-cyclopentyl, dimethyl-cyclopentyl, methyl-cyclohexyl and dimethyl-cyclohexyl. Particular alkylcycloalkyl groups include methyl-cyclopropyl and dimethyl-cyclopropyl.

The term "alkylcycloalkylalkyl" denotes an alkyl group wherein at least one of the hydrogen atoms of the alkyl group is replaced by an alkylcycloalkyl group. Examples of alkylcycloalkylalkyl include methyl-cyclopropylmethyl, dimethyl-cyclopropylmethyl, methyl-cyclopropylethyl, dimethyl-cyclopropylethyl, methyl-cyclobutylmethyl, dimethyl-cyclobutylmethyl, methyl-cyclobutylethyl, dimethyl-cyclobutylethyl, methyl-cylopentylmethyl, dimethyl-cylopentylmethyl, methyl-cyclopentylethyl, dimethyl-cyclopentylethyl, methyl-cyclohexylmethyl, dimethyl-cyclohexylmethyl, methyl-cyclohexylethyl, dimethyl-cyclohexylethyl, methyl-cycloheptylmethyl, dimethyl-cycloheptylmethyl, methyl-cycloheptylethyl, dimethyl-cycloheptylethyl, methyl-cyclooctylmethyl, dimethyl-cyclooctylmethyl, methyl-cyclooctylethyl and dimethyl-cyclooctylethyl.

The term "benzyloxyhaloalkyl" denotes an alkyl wherein one of the hydrogen atoms of the alkyl has been replaced by a benzyloxy group and wherein at least one of the hydrogen atoms of the alkyl has been replaced by a halogen. Examples of benzyloxyhaloalkyl include benzyloxytrifluoroethyl or benzyloxytrifluoropropyl. Particular benzyloxyhaloalkyl is 2,2,2-trifluoro-1-benzyloxyethyl.

The term "cycloalkoxy" denotes a group of the formula —O—R', wherein R' is a cycloalkyl group. Examples of cycloalkoxy group include cyclopropoxy, cyclobutoxy, cyclopentyloxy, cyclohexyloxy, cycloheptyloxy and cyclooctyloxy. Particular cycloalkoxy group is cyclopropoxy.

The term "cycloalkoxyalkyl" denotes an alkyl group wherein at least one of the hydrogen atoms of the alkyl group has been replaced by a cycloalkoxy group. Examples of cycloalkoxyalkyl group include cyclopropoxymethyl, cyclopropoxyethyl, cyclobutoxymethyl, cyclobutoxyethyl, cyclopentyloxymethyl, cyclopentyloxyethyl, cyclohexyloxymethyl, cyclohexyloxyethyl, cycloheptyloxymethyl, cycloheptyloxyethyl, cyclooctyloxymethyl and cyclooctyloxyethyl.

The term "cycloalkyl" denotes a monovalent saturated monocyclic or bicyclic hydrocarbon group of 3 to 10 ring carbon atoms, particularly a monovalent saturated monocyclic hydrocarbon group of 3 to 8 ring carbon atoms. Bicyclic means consisting of two saturated carbocycles having two carbon atoms in common. Particular cycloalkyl groups are monocyclic. Examples for monocyclic cycloalkyl are cyclopropyl, cyclobutanyl, cyclopentyl, cyclohexyl or cycloheptyl. Examples for bicyclic cycloalkyl are bicyclo[2.2.1]heptanyl or bicyclo[2.2.2]octanyl. Particular monocyclic cycloalkyl group is cyclopropyl.

The term "cycloalkylalkyl" denotes an alkyl group wherein at least one of the hydrogen atoms of the alkyl group is replaced by a cycloalkyl group. Examples of cycloalkylalkyl include cyclopropylmethyl, cyclopropylethyl, cyclobutylpropyl and cyclopentylbutyl.

The term "haloalkoxy" denotes an alkoxy group wherein at least one of the hydrogen atoms of the alkoxy group has been replaced by same or different halogen atoms. Examples of haloalkoxy include fluoromethoxy, difluoromethoxy, trifluoromethoxy, trifluoroethoxy, trifluoromethylethoxy, trifluorodimethylethoxy and pentafluoroethoxy. Particular haloalkoxy groups are trifluoromethoxy and trifluoroethoxy. More particular haloalkoxy groups are trifluoromethoxy and 2,2,2-trifluoroethoxy.

The term "haloalkoxyalkyl" denotes an alkyl group wherein at least one of the hydrogen atoms of the alkyl group has been replaced by a haloalkoxy group. Examples of haloalkoxyalkyl include fluoromethoxymethyl, difluoromethoxymethyl, trifluoromethoxymethyl, fluoroethoxymethyl, difluoroethoxymethyl, trifluoroethoxymethyl, fluoromethoxyethyl, difluoromethoxyethyl, trifluoromethoxyethyl, fluoroethoxyethyl, difluoroethoxyethyl, trifluoroethoxyethyl, fluoromethoxypropyl, difluoromethoxypropyl, trifluoromethoxypropyl, fluoroethoxypropyl, difluoroethoxypropyl and trifluoroethoxypropyl.

The term "haloalkyl" denotes an alkyl group wherein at least one of the hydrogen atoms of the alkyl group has been replaced by same or different halogen atoms. Examples of haloalkyl include fluoromethyl, difluoromethyl, trifluoromethyl, trifluoroethyl, trifluoromethylethyl and pentafluoroethyl. Particular haloalkyl groups are trifluoromethyl and trifluoroethyl.

The term "halocycloalkoxy" denotes a cycloalkoxy group wherein at least one of the hydrogen atoms of the cycloalkoxy group has been replaced by same or different halogen atoms, particularly fluoro atoms. Examples of halocycloalkoxyl include fluorocyclopropoxy, difluorocyclopropoxy, fluorocyclobutoxy and difluorocyclobutoxy.

The term "halocycloalkoxyalkyl" denotes an alkyl group wherein at least one of the hydrogen atoms of the alkyl group has been replaced by a halocycloalkoxy. Examples of halocycloalkoxyalkyl include fluorocyclopropoxymethyl, difluorocyclopropoxymethyl, fluorocyclopropoxyethyl, difluorocyclopropoxyethyl, fluorocyclobutoxymethyl, difluorocyclobutoxymethyl, fluorocyclobutoxyethyl and difluorocyclobutoxyethyl.

The term "halocycloalkyl" denotes a cycloalkyl group wherein at least one of the hydrogen atoms of the cycloalkyl group has been replaced by same or different halogen atoms, particularly fluoro atoms. Examples of halocycloalkyl include fluorocyclopropyl, difluorocyclopropyl, fluorocyclobutyl and difluorocyclobutyl.

The term "halocycloalkylalkyl" denotes an alkyl group wherein at least one of the hydrogen atoms of the alkyl group has been replaced by a halocycloalkyl. Examples of halocycloalkylalkyl include fluorocyclopropylmethyl, difluorocyclopropylmethyl, fluorocyclopropylethyl, difluorocyclopropylethyl, fluorocyclobutylmethyl, difluorocyclobutylmethyl, fluorocyclobutylethyl and difluorocyclobutylethyl.

The term "halogen" and "halo" are used interchangeably herein and denote fluoro, chloro, bromo, or iodo. Particular halogens are chloro and fluoro. More particular halogen is fluoro.

The term "hydroxy" denotes a —OH group.

The term "hydroxyhaloalkyl" denotes an alkyl wherein at least one of the hydrogen atoms of the alkyl has been replaced by a hydroxy group and wherein at least one of the hydrogen atoms of the alkyl has been replaced by a halogen. Examples of hydroxyhaloalkyl include hydroxytrifluoroethyl, hydroxytrifluoropropyl and hydroxyhexafluoropropyl. Particular hydroxyhaloalkyl is 2,2,2-trifluoro-1-hydroxyethyl.

The term "hydroxyalkyl" denotes an alkyl group wherein at least one of the hydrogen atoms of the alkyl group has been replaced by a hydroxy group. Examples of hydroxyalkyl include hydroxymethyl, hydroxyethyl, hydroxypropyl, hydroxymethylpropyl and dihydroxypropyl.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, in particular hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particular pharmaceutically acceptable salts of compounds of formula (I) are the hydrochloride salts, methanesulfonic acid salts and citric acid salts.

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

The term "protecting group" (PG) denotes the group which selectively blocks a reactive site in a multifunctional compound such that a chemical reaction can be carried out selectively at another unprotected reactive site in the meaning conventionally associated with it in synthetic chemistry. Protecting groups can be removed at the appropriate point. Exemplary protecting groups are amino-protecting groups, carboxy-protecting groups or hydroxy-protecting groups. Particular protecting groups are the tert-butoxycarbonyl (Boc), benzyloxycarbonyl (Cbz), fluorenylmethoxycarbonyl (Fmoc) and benzyl (Bn). Further particular protecting groups are the tert-butoxycarbonyl (Boc) and the fluorenylmethoxycarbonyl (Fmoc). More particular protecting group is the benzyl group (Bn).

The compounds of formula (I) can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

According to the Cahn-Ingold-Prelog Convention the asymmetric carbon atom can be of the "R" or "S" configuration.

The present invention relates to a compound according to formula (I),

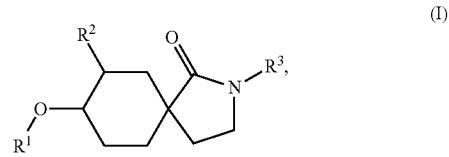

wherein $R^1$ is selected from the group consisting of hydrogen, alkyl and cycloalkyl;

$R^2$ is selected from the group consisting of hydrogen, alkyl, cycloalkyl, cycloalkylalkyl, alkylcycloalkyl, alkylcycloalkylalkyl, alkoxy, alkoxyalkyl, cycloalkoxy, cycloalkoxyalkyl, haloalkyl, haloalkoxy, haloalkoxyalkyl, halocycloalkyl, halocycloalkylalkyl, halocycloalkoxy and halocycloalkoxyalkyl; and $R^3$ is selected from the group consisting of phenyl, pyridinyl, pyrazinyl, pyrimidyl and pyridazinyl, wherein said phenyl, pyridinyl, pyrazinyl, pyrimidyl and pyridazinyl are optionally substituted with one to three substituents independently selected from the group consisting of alkyl, cycloalkyl, cycloalkylalkyl, halogen, haloalkyl, hydroxy, hydroxyalkyl, alkoxy, alkoxyalkyl, haloalkoxy, hydroxyhaloalkyl, alkoxyhaloalkyl and benzyloxyhaloalkyl.

Also an embodiment of the present invention are pharmaceutically acceptable salts or esters of compounds of formula (I), in particular pharmaceutically acceptable salts thereof.

A further embodiment of the present invention are compounds according to formula (I) as described herein, wherein $R^2$ is selected from the group consisting of alkyl, cycloalkyl, alkoxy, alkoxyalkyl, cycloalkoxy, haloalkyl and haloalkoxy.

A particular embodiment of the present invention are compounds according to formula (I) as described herein, wherein $R^2$ is selected from the group consisting of alkyl, alkoxy, haloalkyl and haloalkoxy.

In a further embodiment of the present invention are compounds according to formula (I) as described herein, wherein $R^2$ is selected from the group consisting of alkyl, alkoxy and haloalkoxy.

Another further embodiment of the present invention are compounds according to formula (I) as described herein, wherein $R^2$ is selected from the group consisting of methyl, ethyl, n-propyl, isopropyl, methoxy, ethoxy, n-propoxy, isopropoxy, trifluoromethoxy, and trifluoroethoxy.

Another embodiment of the present invention are compounds according to formula (I) as described herein, wherein $R^2$ is selected from the group consisting of methyl, ethyl, n-propyl, isopropyl, methoxy, ethoxy, n-propoxy, isopropoxy and trifluoroethoxy.

The present invention also relates to compounds according to formula (I) as described herein, wherein $R^2$ is alkyl or haloalkoxy.

A further particular embodiment of the present invention are compounds according to formula (I) as described herein, wherein R² is selected from the group consisting of methyl, ethyl, n-propyl, isopropyl and trifluoroethoxy.

A more particular embodiment of the present invention are compounds according to formula (I) as described herein, wherein R² is alkyl.

Also an embodiment of the present invention are compounds according to formula (I) as described herein, wherein R² is selected from the group consisting of methyl, ethyl, n-propyl and isopropyl.

The present invention also relates to compounds according to formula (I) as described herein, wherein R² is isopropyl.

Another embodiment of the present invention are compounds according to formula (I) as described herein, wherein R² is haloalkoxy.

A further particular embodiment of the present invention are compounds according to formula (I) as described herein, wherein R² is trifluoroethoxy.

A particular embodiment of the present invention are compounds according to formula (I) as described herein, wherein R³ is phenyl optionally substituted with one to three substituents independently selected from the group consisting of alkyl, cycloalkyl, cycloalkylalkyl, halogen, haloalkyl, hydroxy, hydroxyalkyl, alkoxy, alkoxyalkyl, haloalkoxy, hydroxyhaloalkyl, alkoxyhaloalkyl and benzyloxyhaloalkyl.

Also an embodiment of the present invention are compounds according to formula (I) as described herein, wherein R³ is phenyl substituted with one to three substituents independently selected from the group consisting of alkyl, cycloalkyl, cycloalkylalkyl, halogen, haloalkyl, hydroxy, hydroxyalkyl, alkoxy, alkoxyalkyl, haloalkoxy, hydroxyhaloalkyl, alkoxyhaloalkyl and benzyloxyhaloalkyl.

The present invention also relates to compounds according to formula (I) as described herein, wherein R³ is phenyl substituted with one to three substituents independently selected from the group consisting of haloalkoxy, hydroxyhaloalkyl, alkoxyhaloalkyl and benzyloxyhaloalkyl.

Also an embodiment of the present invention are compounds according to formula (I) as described herein, wherein R³ is phenyl substituted with one to three substituents independently selected from the group consisting of trifluoromethoxy, trifluoroethoxy, 2,2,2-trifluoro-1-hydroxyethyl, 2,2,2-trifluoro-1-methoxyethyl and 1-benzyloxy-2,2,2-trifluoroethyl.

Another embodiment of the present invention are compounds according to formula (I) as described herein, wherein R³ is phenyl substituted with one to three substituents independently selected from the group consisting of haloalkoxy and alkoxyhaloalkyl.

The present invention also relates to compounds according to formula (I) as described herein, wherein R³ is phenyl substituted with one substituent independently selected from the group consisting of trifluoromethoxy, trifluoroethoxy and 2,2,2-trifluoro-1-methoxyethyl.

Also an embodiment of the present invention are compounds according to formula (I) as described herein, wherein R³ is phenyl substituted with one haloalkoxy.

Also an embodiment of the present invention are compounds according to formula (I) as described herein, wherein R³ is 4-trifluoromethoxyphenyl or 4-trifluoroethoxyphenyl.

Another embodiment of the present invention are compounds according to formula (I) as described herein, wherein R³ is phenyl substituted with one alkoxyhaloalkyl.

A particular embodiment of the present invention are compounds according to formula (I) as described herein, wherein R³ is phenyl substituted with one 2,2,2-trifluoro-1-methoxyethyl.

A further particular embodiment of the present invention are compounds according to formula (I) as described herein, wherein R¹ is hydrogen.

A further embodiment of the present invention are compounds according to formula (I) as described herein of formula (Ia),

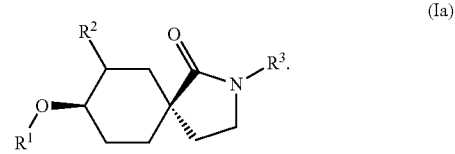

(Ia)

Also a further embodiment of the present invention are compounds according to formula (I) as described herein of formula (Ib),

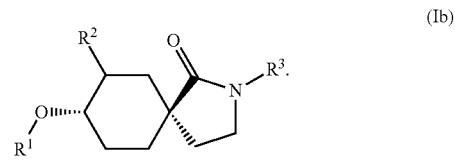

(Ib)

Particular examples of compounds of formula (I) as described herein are selected from the group consisting of:
rac-(5S,7R,8R)-8-hydroxy-7-propyl-2-(4-trifluoromethoxy-phenyl)-2-aza-spiro[4.5]decan-1-one;
rac-(5S,7S,8R)-8-hydroxy-7-isopropyl-2-(4-(trifluoromethoxy)phenyl)-2-azaspiro[4.5]decan-1-one;
rac-(5R,7R,8R)-8-hydroxy-7-isopropoxy-2-(4-(trifluoromethoxy)phenyl)-2-azaspiro[4.5]decan-1-one;
rac-(5R,7R,8R)-7-ethoxy-8-hydroxy-2-(4-(trifluoromethoxy)phenyl)-2-azaspiro[4.5]decan-1-one;
rac-(5R,7R,8R)-8-hydroxy-7-(2,2,2-trifluoroethoxy)-2-(4-(trifluoromethoxy)phenyl)-2-azaspiro[4.5]decan-1-one;
(5R,7R,8R)-8-hydroxy-7-(2,2,2-trifluoroethoxy)-2-(4-trifluoromethoxy-phenyl)-2-aza-spiro[4.5]decan-1-one;
(5S,7S,8S)-8-hydroxy-7-(2,2,2-trifluoroethoxy)-2-(4-trifluoromethoxy-phenyl)-2-aza-spiro[4.5]decan-1-one;
rac-(5R,7R,8R)-8-hydroxy-7-methoxy-2-(4-(trifluoromethoxy)phenyl)-2-azaspiro[4.5]decan-1-one;
rac-(5R,7R,8R)-8-hydroxy-7-propoxy-2-(4-(trifluoromethoxy)phenyl)-2-azaspiro[4.5]decan-1-one;
rac-(5S,7R,8R)-8-hydroxy-7-propyl-2-[4-(2,2,2-trifluoroethoxy)-phenyl]-2-aza-spiro[4.5]decan-1-one;
rac-(5S,7S,8R)-8-hydroxy-7-isopropyl-2-[4-(2,2,2-trifluoro-ethoxy)-phenyl]-2-aza-spiro[4.5]decan-1-one;
rac-(5R,7R,8R)-8-hydroxy-7-(2,2,2-trifluoro-ethoxy)-2-[4-(2,2,2-trifluoro-ethoxy)-phenyl]-2-aza-spiro[4.5]decan-1-one;
rac-(5R,7R,8R)-7-ethoxy-8-hydroxy-2-(4-(2,2,2-trifluoroethoxy)phenyl)-2-azaspiro[4.5]decan-1-one;
rac-(5R,7R,8R)-8-hydroxy-7-isopropoxy-2-(4-(2,2,2-trifluoroethoxy)phenyl)-2-azaspiro[4.5]decan-1-one;
(5R,7R,8R) and (5S,7S,8S)-8-hydroxy-7-isopropoxy-2-(4-((R)-2,2,2-trifluoro-1-methoxyethyl)phenyl)-2-azaspiro[4.5]decan-1-one;
(5R,7R,8R) and (5S,7S,8S)-8-hydroxy-7-(2,2,2-trifluoroethoxy)-2-(4-((R)-2,2,2-trifluoro-1-methoxyethyl)phenyl)-2-azaspiro[4.5]decan-1-one;
(5R,7R,8R) and (5S,7S,8S)-2-(4-((R)-1-(benzyloxy)-2,2,2-trifluoroethyl)phenyl)-8-hydroxy-7-(2,2,2-trifluoroethoxy)-2-azaspiro[4.5]decan-1-one;

(5R,7R,8R) and (5S,7S,8S)-8-hydroxy-7-(2,2,2-trifluoroethoxy)-2-(4-((R)-2,2,2-trifluoro-1-hydroxyethyl)phenyl)-2-azaspiro[4.5]decan-1-one;

and pharmaceutically acceptable salts thereof.

Further particular examples of compounds of formula (I) as described herein are selected from the group consisting of:

rac-(5S,7S,8R)-8-hydroxy-7-isopropyl-2-(4-(trifluoromethoxy)phenyl)-2-azaspiro[4.5]decan-1-one;

(5S,7S,8S)-8-hydroxy-7-(2,2,2-trifluoroethoxy)-2-(4-trifluoromethoxy-phenyl)-2-aza-spiro[4.5]decan-1-one;

rac-(5S,7S,8R)-8-hydroxy-7-isopropyl-2-[4-(2,2,2-trifluoro-ethoxy)-phenyl]-2-aza-spiro[4.5]decan-1-one;

(5R,7R,8R) and (5S,7S,8S)-8-hydroxy-7-(2,2,2-trifluoroethoxy)-2-(4-((R)-2,2,2-trifluoro-1-methoxyethyl)phenyl)-2-azaspiro[4.5]decan-1-one;

and pharmaceutically acceptable salts thereof.

Processes for the manufacture of compounds of formula (I) as described herein are an object of the invention.

The preparation of compounds of formula (I) of the present invention may be carried out in sequential or convergent synthetic routes. Syntheses of the invention are shown in the following general schemes. The skills required for carrying out the reaction and purification of the resulting products are known to those persons skilled in the art. In case a mixture of enantiomers or diastereoisomers is produced during a reaction, these enantiomers or diastereoisomers can be separated by methods described herein or known to the man skilled in the art such as e.g. chiral chromatography or crystallization. The substituents and indices used in the following description of the processes have the significance given herein. Relative configuration on the bi- and tricyclic backbone structures is indicated with the appropriate stereodescriptors; if a compound is obtained as a racemic mixture it is indicated with the descriptor "rac" in conjunction with the name.

Scheme 1 outlines the synthesis of some key intermediates used in processes described therein.

Scheme 1

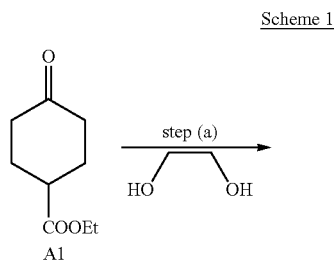

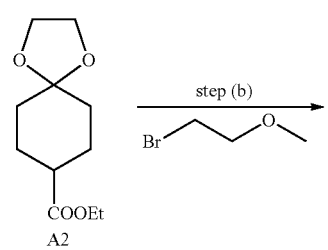

Commercially available ketone A1 can be protected for example as a ketal (step (a)) to give the compound A2 according to methods well known in the literature. Ketal A2 is then alkylated at the appropriate position by treatment with a suitable base such as lithium diisopropylamide, lithium or sodium hexamethyldisilazane, potassium tert-butylate or the like in an appropriate solvent such as THF, DMF, diethylether or the like followed by addition of the appropriate electrophile 1-bromo-2-methoxyethane to give compound A3 (step (b)). A3 can be isolated if desired or the ketal group can be removed (step (c)) during the workup of reaction step (b). Treatment of crude A3 with a strong aqueous mineral acid such as HCl, $H_2SO_4$, HBr or the like at various temperatures ranging from −15° C. to 100° C. until hydrolysis of the ketal protecting group is completed (step(c)) gives compound A4. Starting from intermediate A4, mixtures of cis and trans alcohols A5 can be prepared via reduction of the carbonyl group (step (d)) with various reducing agents such as for example $NaBH_4$, $LiBH_4$, SMEAH, L-selectride or similar in an appropriate solvent such as MeOH, EtOH, THF, diethylether and the like and at various temperatures ranging from −78° C. to the reflux temperature.

Subsequent formation of the 2-aza-spiro[4.5]decan-1-one backbone can be achieved as outlined in Scheme 2, step (e) by treatment of A5 with an appropriate compound of formula A6 and an appropriate Lewis acid such as $(CH_3)_2AlCl$ in an suitable solvent such as toluene, benzene, chloroform, dioxane or the like at various temperatures ranging from 0 to 150° C. to provide the key intermediates of formula A7.

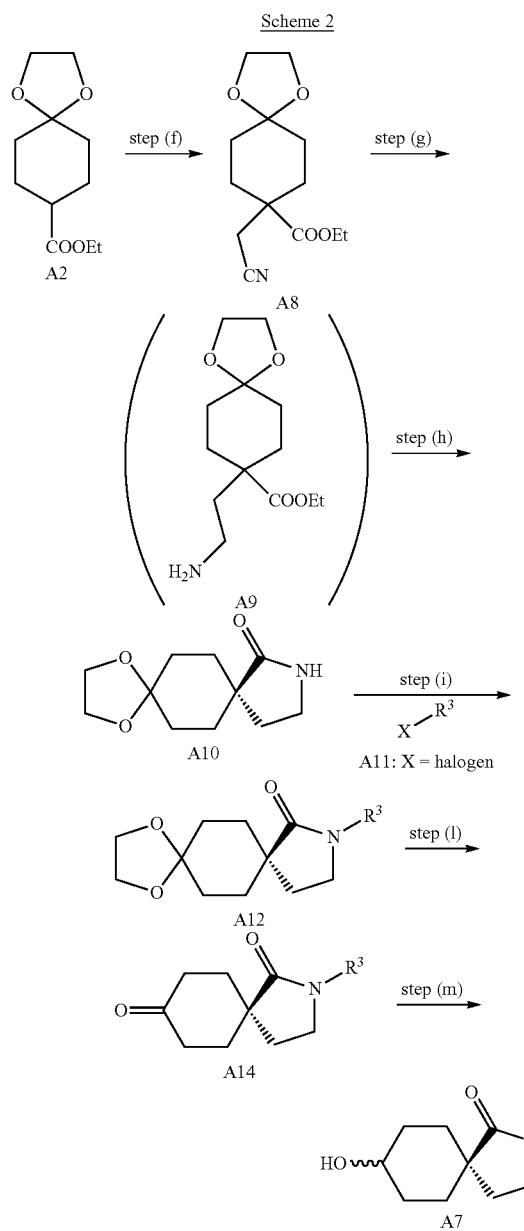

An alternative route to provide intermediates A7 is outlined in Scheme 2. In this case, protected starting material A2 is alkylated with a suitable α-haloacetonitrile in the presence of a suitable base such as LDA, LiHMDS, NaH or the like in an appropriate solvent such as THF, ether or similar to provide nitrile A8 (step (f)). In order to gain access to lactam A10, the nitrile group is reduced to the primary amine (intermediate A9) for example by catalytic hydrogenation in the presence of a suitable catalyst such as $PtO_2$, or the like (step (g)). Suitable additives such as acids or bases may be needed to prevent unwanted side reactions in this particular reaction step. Depending on the workup conditions in reaction step (g) it may not be required to isolate intermediate A9 since cyclization to lactam A10 (step (h)) may readily occur. If cyclization of A9 is inhibited for example by the presence of a strong acid, then liberation of the amine group by a base is appropriate to specifically perform step (h) at room temperature or with heating. With intermediate A10, it is possible to introduce a variety of $R^3$ groups to the lactam nitrogen (step (i)). Such transformations are possible with copper- or palladium-catalysed coupling reactions with intermediates A11, providing intermediates A12. An example of such a transformation is a classic Goldberg reaction (for methodology see for example: Buchwald et al., JACS 2002, 124, page 7421). Suitable conditions using appropriate intermediates A11 include, for example: CuI and, for example, N,N'-dimethylethylenediamine as ligand and $K_3PO_4$ as base in a solvent such as DMF or palladium(II) acetate as catalyst and, for example, bis(diphenylphosphino)-ferrocene (DPPF) as ligand, sodium tert-butoxide as a base in a solvent such as toluene.

Intermediate A12 can be converted to ketone A14 by acidic hydrolysis; for example by treatment with an aqueous mineral acid such as HCl, $H_2SO_4$ or the like (step (l)). Subsequent reduction of the keto carbonyl group of A14 can be achieved as described earlier for intermediate A4, providing again mixtures of cis and trans alcohols A7 (step (m)). This step can be carried out with various reducing agents such as for example $NaBH_4$, $LiBH_4$, SMEAH, L-selectride or similar in an appropriate solvent such as MeOH, EtOH, THF, diethylether and the like and at various temperatures ranging from −78° C. to the reflux temperature.

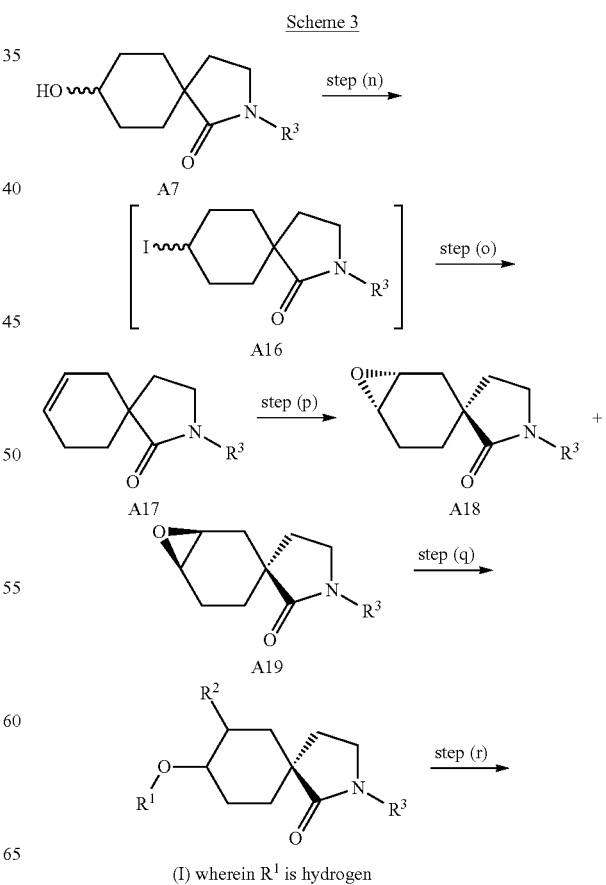

-continued

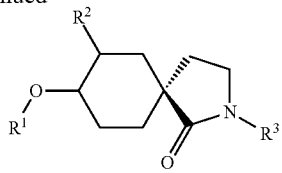

(I) wherein R¹ is alkyl or cycloalkyl

Subsequent iodination (step (n)) of alcohol intermediate A7 can be achieved for example by treatment of the starting material A7 with a mixture of iodine and triphenylphosphine in a suitable solvent such as dichloromethane (DCM), chloroform or the like to provide a compound of formula A16, which may be isolated if required. Under certain conditions, the transformation proceeds directly to unsaturated intermediate A17 or to mixtures of A16 and A17. If A16 is isolated, complete elimination of the iodine can be achieved by treatment of A16 with an organic base such a triethylamine, DBU, DMAP, or the like in a suitable solvent such as THF, ether, DCM or the like at various temperatures ranging from 0° C. to 100° C. (step (o)). Subsequent treatment of A17 with m-CPBA in a suitable solvent such as DCM or the like (step (p)) provides cis and trans epoxides A18 and A19, respectively. Cis- and trans-epoxides can be isolated in pure form using separation techniques known to those skilled in the art. The appropriate epoxide (A18 or A19) is then treated with the desired nucleophile to provide compounds of formula (I). For step (q), if R² is alkyl, cycloalkyl, cycloalkylalkyl, alkylcycloalkyl, alkylcycloalkylalkyl, alkoxyalkyl, cycloalkoxyalkyl, haloalkyl, haloalkoxyalkyl, halocycloalkyl, halocycloalkylalkyl or halocycloalkoxyalkyl, it can be introduced as a Grignard or lithium reagent in the presence of suitable additives such as copper in various solvents and at suitable temperatures. In case R² is alkoxy, cycloalkoxy, haloalkoxy or halocycloalkoxy, then it can be introduced for example by treatment of R²—H with a suitable base such as sodium hydride or potassium tert-butoxide or the like or, alternatively, by activating epoxide A18 or A19 with a suitable Lewis acid such as erbium(III) trifluoromethanesulfonate, wherein R²—H can be used as the solvent when appropriate. Compounds of formula (I), wherein R¹ is alkyl or cycloalkyl can be prepared by method known to the man skilled in the art (step (r)).

Also an embodiment of the present invention is a process to prepare a compound of formula (I) as defined above comprising the reaction of a) a compound of formula (II) in the presence of a reducing agent, particularly NaBH₄;

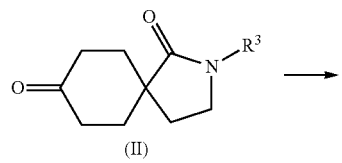

In particular in a solvent, particularly MeOH and PrOH, at a temperature comprised between −78° C. and reflux, particularly comprised between −10° C. and RT, wherein R¹ and R² are hydrogen and R³ is as defined herein;

b) a compound of formula (III) in the presence of a compound of formula (IV);

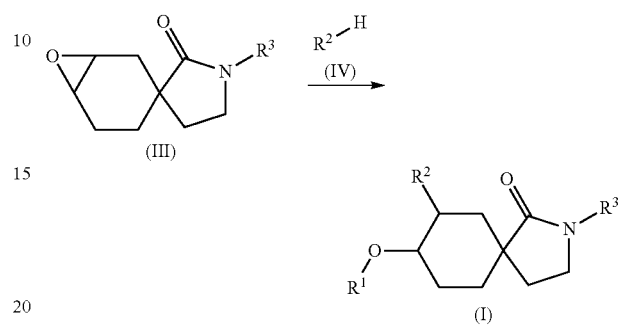

In particular in the presence of a base, particularly sodium hydride and potassium tert-butoxide, in the presence or not of erbium(III) trifluoromethanesulfonate, in a solvent, particularly R²—H wherein R¹ is hydrogen, R² is alkoxy, cycloalkoxy, haloalkoxy or halocycloalkoxy, more particularly alkoxy and R³ is as defined herein;

c) a compound of formula (III) in the presence of a compound of formula (V);

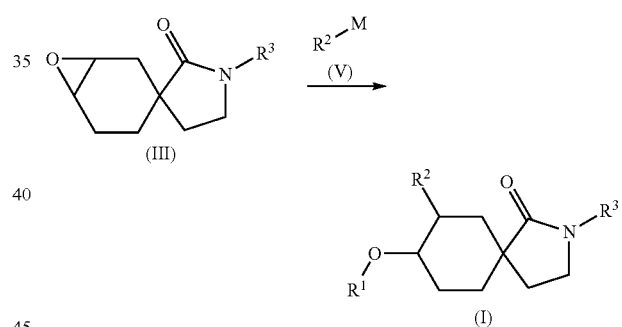

In particular in the presence or not of a copper additives, particularly CuCN, in a solvent, particularly diethyl ether and tetrahydrofuran, at a temperature comprised between −78° C. and reflux, particularly comprised between −78° C. and 0° C., wherein R¹ is hydrogen, R² is alkyl, cycloalkyl, cycloalkylalkyl, alkylcycloalkyl, alkylcycloalkylalkyl, alkoxyalkyl, cycloalkoxyalkyl, haloalkyl, haloalkoxyalkyl, halocycloalkyl, halocycloalkylalkyl or halocycloalkoxyalkyl, R³ is as defined herein, M is MgCl, MgBr or Li. or d) a compound of formula (Ic) in the presence of a compound of formula (VI);

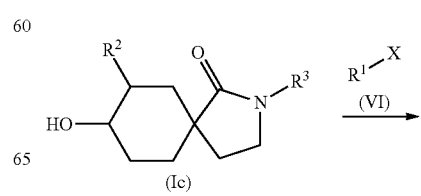

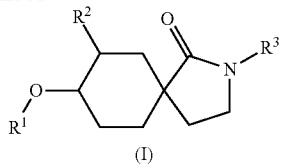

In particular in the presence of a base, particularly sodium hydride and potassium tert-butoxide, in a solvent, particularly, dichloromethane, diethyl ether or tetrahydrofuran at a temperature comprised between −78° C. and reflux, wherein $R^1$ is alkyl or cyloalkyl, $R^2$ and $R^3$ are as defined herein, X is halogen, particularly chloro and bromo, mesylate or tosylate.

Also an object of the present invention is a compound according to formula (I) as described herein for use as therapeutically active substance.

Likewise an object of the present invention is a pharmaceutical composition comprising a compound according to formula (I) as described herein and a therapeutically inert carrier.

Also an object of the present invention is the use of a compound according to formula (I) as described herein for the treatment or prophylaxis of illnesses which are caused by disorders associated with the enzyme hormone-sensitive lipase.

The present invention relates to the use of a compound according to formula (I) as described above for the treatment or prophylaxis of diabetes, metabolic syndrome, dyslipidemia, atherosclerosis, obesity, cardiovascular diseases, myocardial dysfunction, inflammation, nonalkoholic fatty liver disease or nonalkoholic steatohepatitis The present invention particularly relates to the use of a compound according to formula (I) as described above for the treatment or prophylaxis of diabetes, metabolic syndrome, dyslipidemia, atherosclerosis or obesity.

A particular embodiment of the present invention is the use of a compound according to formula (I) as described above for the treatment or prophylaxis of diabetes.

A further particular embodiment of the present invention is the use of a compound according to formula (I) as described above for the treatment or prophylaxis of diabetes Type II.

Also an embodiment of the present invention is the use of a compound according to formula (I) as described above for the treatment or prophylaxis of cardiovascular diseases, myocardial dysfunction, inflammation, nonalkoholic fatty liver disease or nonalkoholic steatohepatitis.

A particular embodiment of the present invention is the use of a compound according to formula (I) as described above for the treatment or prophylaxis of nonalkoholic fatty liver disease or nonalkoholic steatohepatitis.

The present invention also relates to the use of a compound according to formula (I) as described above for the preparation of a medicament for the treatment or prophylaxis of diabetes, metabolic syndrome, dyslipidemia, atherosclerosis, obesity, cardiovascular diseases, myocardial dysfunction, inflammation, nonalkoholic fatty liver disease or nonalkoholic steatohepatitis.

The present invention particularly relates to the use of a compound according to formula (I) as described above for the preparation of a medicament for the treatment or prophylaxis of diabetes, metabolic syndrome, dyslipidemia, atherosclerosis or obesity.

A particular embodiment of the present invention is the use of a compound according to formula (I) as described above for the preparation of medicaments for the treatment or prophylaxis of diabetes.

A further particular embodiment of the present invention is the use of a compound according to formula (I) as described above for the preparation of medicaments for the treatment or prophylaxis of diabetes Type II.

Also an embodiment of the present invention is the use of a compound according to formula (I) as described above for the preparation of a medicament for the treatment or prophylaxis of cardiovascular diseases, myocardial dysfunction, inflammation, nonalkoholic fatty liver disease or nonalkoholic steatohepatitis.

A particular embodiment of the present invention is the use of a compound according to formula (I) as described above for the preparation of a medicament for the treatment or prophylaxis of nonalkoholic fatty liver disease or nonalkoholic steatohepatitis.

The present invention particularly relates to a compound according to formula (I) as described above for the treatment or prophylaxis of diabetes, metabolic syndrome, dyslipidemia, atherosclerosis, obesity, cardiovascular diseases, myocardial dysfunction, inflammation, nonalkoholic fatty liver disease or nonalkoholic steatohepatitis.

A particular embodiment of the present invention is a compound according to formula (I) as described above for the treatment or prophylaxis of diabetes, metabolic syndrome, dyslipidemia, atherosclerosis or obesity.

A further particular embodiment of the present invention is a compound according to formula (I) as described above for the treatment or prophylaxis of diabetes.

Also a further particular embodiment of the present invention is a compound according to formula (I) as described above for the treatment or prophylaxis of diabetes Type II.

Also a particular embodiment of the present invention is a compound according to formula (I) as described above for the treatment or prophylaxis of cardiovascular diseases, myocardial dysfunction, inflammation, nonalkoholic fatty liver disease or nonalkoholic steatohepatitis.

A further particular embodiment of the present invention is a compound according to formula (I) as described above for the treatment or prophylaxis of nonalkoholic fatty liver disease or nonalkoholic steatohepatitis.

Also an object of the invention is a method for the treatment or prophylaxis of diabetes, metabolic syndrome, dyslipidemia, atherosclerosis, obesity, cardiovascular diseases, myocardial dysfunction, inflammation, nonalkoholic fatty liver disease or nonalkoholic steatohepatitis, which method comprises administering an effective amount of a compound according to formula (I) as described above.

Also a particular object of the invention is a method for the treatment or prophylaxis of diabetes, metabolic syndrome, dyslipidemia, atherosclerosis or obesity, which method comprises administering an effective amount of a compound according to formula (I) as described above.

A particular embodiment of the present invention is a method for the treatment or prophylaxis of diabetes, which method comprises administering an effective amount of a compound according to formula (I) as described above.

A further particular embodiment of the present invention is a method for the treatment or prophylaxis of diabetes Type II, which method comprises administering an effective amount of a compound according to formula (I) as described above.

Also an embodiment of the present invention is a method for the treatment or prophylaxis of cardiovascular diseases, myocardial dysfunction, inflammation, nonalkoholic fatty liver disease or nonalkoholic steatohepatitis, which method comprises administering an effective amount of a compound according to formula (I) as described above.

Also a further embodiment of the present invention is a method for the treatment or prophylaxis of nonalkoholic fatty liver disease or nonalkoholic steatohepatitis, which method comprises administering an effective amount of a compound according to formula (I) as described above.

A further object of the present invention comprises a compound according to formula (I) as described herein, when manufactured according to any one of the described processes.

Assay Procedures

Production of Human Full Length Hormone Sensitive Lipase-His[6]:
1) Cloning: cDNA was prepared from commercial human brain polyA+RNA and used as a template in overlapping PCR to generate a full length human HSL ORF with a 3'-His6 tag. This full length insert was cloned into the pFast-BAC vector and the DNA-sequence of several single clones was verified. DNA from a correct full length clone with the 3'His6 tag was used to transform the *E. coli* strain DH10BAC. Resulting bacmid DNA was used to generate a titered baculovirus stock for protein generation. The sequence of the encoded HSL conforms to Swissprot entry Q05469, with the additional C-terminal His6-tag.
2) Protein purification: Culture: 5.5 L, High 5 cells expressing human full length HSL-His[6], 48 hr., containing 25 μM E-64. Cell count: $1.78 \times 10^{10}$ cells/ml, 90% viable. Cells were thawed. On ice, cells were suspended in Base Buffer containing 10% glycerol, 25 mM Tris-Cl, 300 mM NaCl, 10 mM imidazole, 10 mM 2-mercaptoethanol, 2 μg pepstatin/ml, 2 μg leupeptin/ml, 2 μg antipain/ml, pH 8.0 at 4° C. in a final volume of 475 ml with $3.75 \times 10^7$ cells/ml. Sanitation was done at 3×30 sec., Lubrol PX was added to 0.2% final concentration followed by stirring for 15 min. at 4° C. and centrifugation at 25 k×g, 60 mM, 4° C. Soluble proteins were mixed with 60 ml of pre-washed and equilibrated Ni-NTA Agarose (Qiagen 30210) followed by tumbling end-over-end, 45 mM., 4° C., centrifugation 1000 rpm 5 min and letting resin settle 5 min. Supernatant was removed, the resin washed in the centrifuge vessel using 5 volumes of Base Buffer containing 0.2% Lubrol PX. Centrifugation was done again, then the supernatant discarded. The resin wass poured onto a 0.8 μm membrane in a disposable filter unit (Nalge 450-0080), and washed with 5 volumes of Base Buffer containing 0.2% Lubrol PX. It was then washed with 30 volumes of Base Buffer containing 60 mM imidazole pH 7.5 at 4° C. The protein was eluated with 5 volumes of 25 mM Tris-Cl, 300 mM NaCl, 200 mM imidazole, 10 mM 2-mercaptoethanol, pH 7.5 at 4° C. by tumbling resin with buffer end-over-end, 30 min., 4° C. The resin was captured on a 0.2 μm membrane disposable filter unit (Millipore SCGP U02 RE) and the eluate collected in the reservoir. The eluate was concentrated using a 30 k MWCO centrifugal filter device (Sartorius Vivascience Vivacell 100, VC1022), to 20 ml. It was then dialyzed overnight at 4° C., two times against 2 L of 10% glycerol, 25 mM Tris-Cl, 300 mM NaCl, 0.2 mM EDTA, 0.2 mM DTT, pH 7.5 at 4° C. The protein was filtered using a 0.22 μm disposable filter unit (Millipore SCGP00525). The protein concentration was calculated from absorbance at 280 nm, using 280=0.67 cm$^{-1}$ mg-1. Yield was 235 mg, total. The protein was stored at −80° C.

Human Hormone-Sensitive Lipase (HSL) Enzyme Inhibition Assay:

HSL enzyme activity was measured by a colorimetric assay using 2,3-dimercapto-1-propanol tributyrate (Aldrich, St. Louis, Mo.) as a substrate. Typically, 1.5 mM 2,3-dimercapto-1-propanol tributyrate (DMPT) in 100 mM MOPS, pH 7.2, 0.2 mg/ml fatty acid-free BSA was prepared by sonication at 4° C. to homogenous suspension. Test compounds (2 mM stock in DMSO) were diluted 3 fold in series in DMSO. Compound solutions were diluted 24 fold in 1.5 mM DMPT containing solution and 18 ul per well was added to 384-well microplates (Corning Costar). Twelve microliters per well of human HSL (15 ug/ml) was added and the reaction mixture was incubated at 37° C. for 20 minutes. Six microliters of 12 mM dithio-bis-(2-nitrobenzoic acid) (DTNB) in DMSO plus 1.2% SDS and 0.6% Triton X-100 were added and the mixture was incubated at room temperature for 15 minutes. Product production was monitored by reading absorbance at 405 nm on an Envision Reader (PerkinElmer Life and Analytical Sciences, Shelton, Conn.).

Cellular Assay:

The following assay was used to measure the effect of the compounds to inhibit lipolysis in intact cells (adipocytes). 3T3-L1 pre-adipocyte cells were plated into 96-well plates at a density of 20,000 cells/well in 200 ul growth media (DMEM/10% Calf Serum/1× antibiotic-antimycotic) until confluent. At 48 hours post-confluency, the medium was removed and the cells were differentiated into adipocytes with differentiation medium (DMEM/10% FBS/1× Antibiotic-Antimycotic PLUS: 1 uM IBMX (3-Isobutyl-1-methylxanthine) Inhibitor of phosphodiesterases, 1 uM Dexamethasone, 1 uM Rosiglitazone, 10 ug/ml Insulin). The cells were incubated in said medium for 3 days and then medium was changed to post-differentiation medium (DMEM/10% FBS PLUS: 10 ug/ml Insulin) and the cells were incubated for an additional 3 days. The medium was then changed to maintenance media (DMEM/10% FBS). The cells were fed every 3 days with maintenance media until use. The lipolysis assay may be performed on day 9-14 after the initiation of differentiation in 96 well plates.

The lipolysis assay was performed as follows. The adipocytes were washed 2× with 200 ul Krebs Ringer Bicarbonate Hepes buffer (KRBH)/3% BSA. Test compounds were at 10 mM in DMSO and were initially diluted to 5 mM in DMSO. They were then serially diluted 5-fold in DMSO (5 mM to 320 μM). Each compound was then diluted 200-fold into KRBH/ 3% BSA (0.5% DMSO final). The resulting solutions range from 25 uM to 1.6 μM final. One hundred fifty ul of the diluted compounds were added to each well (in triplicate) and the cells were preincubated 30 min at 37° C. Forskolin (50 uM final) was added to the wells and the cells were incubated 120 minutes at 37° C. One hundred ul was collected into a new 96-well plate for glycerol analysis. The amount of glycerol produced was determined using a glycerol determination kit (Sigma).

| Examples | HSL hum IC50 (uM) |
|---|---|
| 1 | 0.067 |
| 2 | 0.0162 |
| 3 | 0.189 |
| 4 | 0.198 |
| 5 | 0.0664 |
| 6 | 0.158 |
| 7 | 0.0421 |
| 8 | 0.343 |
| 9 | 0.0733 |
| 10 | 0.0037 |

| Examples | HSL hum IC50 (uM) |
|---|---|
| 11 | 0.0024 |
| 12 | 0.35 |
| 13 | 0.994 |
| 14 | 0.422 |
| 15 | 0.136 |
| 16 | 0.175 |
| 17 | 1.067 |
| 18 | 0.185 |

Compounds of formula (I) and their pharmaceutically acceptable salts or esters thereof as described above have $IC_{50}$ values between 0.0001 uM and 1000 uM, particular compounds have $IC_{50}$ values between 0.001 uM and 500 uM, further particular compounds have $IC_{50}$ values between 0.001 uM and 5 uM. These results have been obtained by using the foregoing HSL enzyme inhibition assay (uM means microMolar).

The compounds of formula (I) and their pharmaceutically acceptable salts can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions).

The compounds of formula (I) and their pharmaceutically acceptable salts can be processed with pharmaceutically inert, inorganic or organic adjuvants for the production of tablets, coated tablets, dragées and hard gelatin capsules. Lactose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should be appropriate. It will, however, be clear that the upper limit given herein can be exceeded when this is shown to be indicated.

The invention is illustrated hereinafter by Examples, which have no limiting character.

In case the preparative examples are obtained as a mixture of enantiomers, the pure enantiomers can be separated by methods described herein or by methods known to the man skilled in the art, such as e.g. chiral chromatography or crystallization.

EXAMPLES

Example 1 rac-(5S,7R,8R)-8-Hydroxy-7-propyl-2-(4-trifluoromethoxy-phenyl)-2-aza-spiro[4.5]decan-1-one

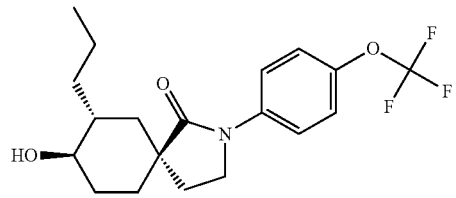 [SMILES: CCC[C@@H]1C[C@@]2(CC[C@H]1O)CCN(c1ccc(OC(F)(F)F)cc1)C2=O]

Step 1: 1,4-Dioxa-spiro[4.5]decane-8-carboxylic acid ethyl ester

Ethyl-cyclohexanone-4-carboxylate (54.8 g) was dissolved in toluene (120 mL). Then, ethylene glycol (24.8 mL) and toluene-4-sulfonic acid monohydrate (612 mg) were added to the reaction mixture. The mixture was refluxed over night and water was removed azeotropically with a Dean-Stark apparatus. The reaction mixture was cooled, poured into ice/water and basified with 2M aqueous NaOH to pH 9. The aqueous layer was extracted two times with ethyl acetate. The combined organic layers were washed with brine, dried over $Na_2SO_4$, filtered and the solvent was evaporated. The residue was purified by flash chromatography (silica gel, gradient of ethyl acetate in heptane) to give the title compound as a light yellow liquid (39.5 g, 57%). MS (ESI)=215.3 ($MH^+$).

Step 2: 1-(2-Methoxy-ethyl)-4-oxo-cyclohexanecarboxylic acid ethyl ester

A solution of 1,4-dioxa-spiro[4.5]decane-8-carboxylic acid ethyl ester (39.5 g) in THF (200 mL) was added dropwise over a period of 45 minutes at −5° C. (ice/methanol bath) to a solution of lithiumdiisopropylamide (2M in THF, 184.3 mL) in THF (300 mL). Stirring was continued for 2.5 hours at 0° C. The reaction mixture was cooled to −5° C. and 2-bromoethyl-methylether (34.6 mL) was added dropwise over a period of 30 minutes. Stirring was continued for 12 hours at RT. The reaction mixture was cooled to 0° C. and aqueous HCl (25%, 300 mL) was added dropwise over a period of 45 minutes to reach pH 1. Stirring was continued for 2 hours at RT. The reaction mixture was poured into ice/water and extracted two times with ethyl acetate. The combined organic layers were washed with brine, dried over $Na_2SO_4$, filtered and the solvent was evaporated. The residue was purified by flash chromatography (silica gel, gradient of ethyl acetate in heptane) to give the title compound as a yellow liquid (25.2 g, 60%). MS (EI)=288.0 ($M^+$).

Step 3: cis/trans-4-Hydroxy-1-(2-methoxy-ethyl)-cyclohexanecarboxylic acid ethyl ester 1-(2-Methoxy-ethyl)-4-oxo-cyclohexanecarboxylic acid ethyl ester (1.60 g) was dissolved in 2-propanol (25 mL). The mixture was cooled to 0° C. and sodium borohydride (331 mg) was added in 3 portions over 10 minutes. Stirring was continued for 2 hours at 0° C. The reaction mixture was poured into ice/water and extracted two times with ethyl acetate. The combined organic layers were washed with brine, dried over $Na_2SO_4$, filtered and the solvent was evaporated. The title compound was obtained as an inseparable mixture of cis and trans diastereomeres in an approximate ratio of 3/1 as a light yellow liquid (1.58 g, 98%). This mixture was used without further purification. MS (EI)=230.0 ($M^+$).

Step 4: 8-Hydroxy-2-(4-trifluoromethoxy-phenyl)-2-aza-spiro[4.5]decan-1-one 4-(Trifluoromethoxy)-aniline (3.05 mL, [CAS Reg. No. 461-82-5]) was added to a solution of cis/trans-4-hydroxy-1-(2-methoxy-ethyl)-cyclohexanecarboxylic acid ethyl ester (3.49 g) in toluene (80 mL). The mixture was stirred for 10 minutes at RT. Then, dimethylaluminiumchloride (1M in hexane, 30.3 mL) was added dropwise over a period of 20 minutes. The reaction mixture was stirred at reflux for 4.5 hours. The mixture was cooled, poured into ice/water and extracted two times with ethyl acetate. The combined organic layers were washed with brine, dried over $Na_2SO_4$, filtered and the solvent was evaporated. The residue was purified by flash chromatography (silica gel, gradient of ethyl acetate in heptane) to give the title compound as a colorless solid (3.96 g, 79%). MS (ESI)=330.1 ($MH^+$).

Step 5: 2-(4-Trifluoromethoxy-phenyl)-2-aza-spiro[4.5]dec-7-en-1-one 8-hydroxy-2-(4-(trifluoromethoxy)phenyl)-2-azaspiro[4.5]decan-1-one (1.0 g), imidazole (438 mg) and triphenylphosphine (2.72 g) were dissolved in dichloromethane (30 mL) under argon. A solution of iodine (1.59 g) in dichloromethane (25.0 mL) was added dropwise over a period of 10 minutes to the reaction mixture and stirring was continued for 20 hours at RT. The reaction mixture was poured into ice/water and basified with saturated $NaHCO_3$ solution. The aqueous phase was then extracted two times with ethyl acetate and the organic layers were washed brine, dried over $Na_2SO_4$, filtered and the solvent was evaporated. The crude material was purified by flash chromatography (gradient of ethyl acetate in heptane) to provide an inseparable mixture of 2-(4-trifluoromethoxy-phenyl)-2-aza-spiro[4.5]dec-7-en-1-one and 8-iodo-2-(4-trifluoromethoxy-phenyl)-2-aza-spiro[4.5]decan-1-one (1.06 g).

This mixture was dissolved in tetrahydrofuran (10 mL) and 1,8-diazabicyclo[5.4.0]undec-7-ene (DBU, 441 mg) was added to the reaction mixture. The mixture was refluxed for 18 hours. The reaction mixture was poured into ice/water and was acidified with 1M HCl solution. The aqueous phase was then extracted two times with ethyl acetate and the organic layers were washed brine, dried over $Na_2SO_4$, filtered and the solvent was evaporated. The crude material was purified by flash chromatography (gradient of ethyl acetate in heptane) to provide the title compound as a colorless solid (676 mg). MS (ESI): 312.1 ($MH^+$).

Step 6: rac-(1R,3R,6S)-1'-(4-(Trifluoromethoxy)phenyl)-7-oxaspiro[bicyclo[4.1.0]heptane-3,3'-pyrrolidin]-2'-one and rac-(1S,3R,6R)-1'-(4-(trifluoromethoxy)phenyl)-7-oxaspiro[bicyclo[4.1.0]heptane-3,3'-pyrrolidin]-2'-one 2-(4-(trifluoromethoxy)phenyl)-2-azaspiro[4.5]dec-7-en-1-one (300 mg) was dissolved in dichloromethane (15.0 mL) under argon. The reaction mixture was cooled to 0° C. in an ice-bath and a solution of 3-chloroperbenzoic acid (70%, 249 mg) in dichloromethane (15.0 mL) was added dropwise over a period of 5 minutes. Stirring was continued for 2 hours at 0° C. and then for 20 hours at RT. Next, sodium hydrogen sulfite solution (38-40%, 10 mL) was added and the resulting mixture was stirred again for 30 minutes at RT. The reaction mixture was poured into ice/water and basified with saturated $NaHCO_3$ solution. The aqueous phase was then extracted two times with ethyl acetate and the organic layers were washed brine, dried over $Na_2SO_4$, filtered and the solvent was evaporated. The crude material was purified by flash chromatography (gradient of heptane in ethyl acetate) to give two diastereomeric epoxides in pure form:

The trans epoxide rac-(1R,3R,6S)-1'-(4-(trifluoromethoxy)phenyl)-7-oxaspiro[bicyclo[4.1.0]heptane-3,3'-pyrrolidin]-2'-one with $R_f$=0.48 (silica gel, heptane/ethyl acetate 1:1): 153 mg of a white solid. MS (ESI): 328.3 ($MH^+$).

The cis epoxide rac-(1S,3R,6R)-1'-(4-(trifluoromethoxy)phenyl)-7-oxaspiro[bicyclo[4.1.0]heptane-3,3'-pyrrolidin]-2'-one with $R_f$=0.25 (silica gel, heptane/ethyl acetate 1:1): 158 mg of a white solid. MS (ESI): 328.3 ($MH^+$).

Step 7: rac-(5S,7R,8R)-8-Hydroxy-7-propyl-2-(4-trifluoromethoxy-phenyl)-2-aza-spiro[4.5]decan-1-one Dry cuprous cyanide (30.1 mg) was placed in a 25 mL 3-neck flask that was then evacuated and purged with argon three times. Then, tetrahydrofuran (2.0 mL) was added and the slurry was cooled to −78° C. in an acetone/$CO_2$-bath. 2-Thienyllithium was prepared in a separate 10 mL 3-neck flask from thiophene (30.1 mg) dissolved in tetrahydrofuran (2.0 mL) by addition of n-butyllithium (1.6M in hexanes, 220 μL) at −30° C.; with stirring being continued for 30 minutes. Then, the solution of 2-thienyllithium was added to the CuCN slurry at −78° C. Stirring was continued at −78° C. for 10 minutes.

Propylmagnesium chloride solution in diethyl ether (2M, 176 μL) was added dropwise over a period of 5 minutes to the mixture. The reaction mixture was warmed up to room temperature. After re-cooling to −78° C., a solution of the cis epoxide rac-(1S,3R,6R)-1'-(4-(trifluoromethoxy)phenyl)-7-oxaspiro[bicyclo[4.1.0]heptane-3,3'-pyrrolidin]-2'-one (100 mg) in tetrahydrofuran (2.0 mL) was added dropwise over a period of 5 minutes. Stirring was continued for 15 minutes at −78° C. The mixture was warmed up to 0° C. for 45 minutes and then to room temperature for 16 hours. The reaction mixture was poured into ice/water and acidified with saturated $NH_4Cl$ solution. The aqueous phase was then extracted two times with ethyl acetate and the organic layers were washed brine, dried over $Na_2SO_4$, filtered and the solvent was evaporated. The crude material was purified two times by two subsequent flash chromatographies (gradient of ethyl acetate in heptane, then gradient of acetonitrile in dichlormethane) to give the title compound rac-(5S,7R,8R)-8-hydroxy-7-propyl-2-(4-trifluoromethoxy-phenyl)-2-aza-spiro[4.5]decan-1-one as a colorless liquid (18 mg). MS (ESI): 372.2 ($MH^+$).

Example 2 rac-(5S,7S,8R)-8-hydroxy-7-isopropyl-2-(4-(trifluoromethoxy)phenyl)-2-azaspiro[4.5]decan-1-one

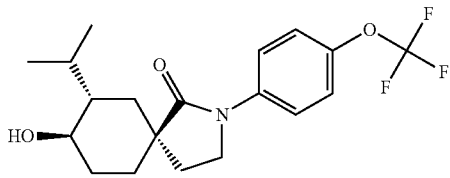 [SMILES: CC(C)[C@@H]1C[C@@]2(CC[C@H]1O)CCN(c1ccc(OC(F)(F)F)cc1)C2=O]

This material was obtained in analogy to Example 1, step 7 from cis 1'-(4-trifluoromethoxyphenyl)-spiro[7-oxabicyclo[4.1.0]heptane-3,3'-pyrrolidine-2'-one by using isopropylmagnesium bromide as the appropriate Grignard reagent. rac-(5S,7S,8R)-8-Hydroxy-7-isopropyl-2-(4-(trifluoromethoxy)phenyl)-2-azaspiro[4.5]decan-1-one was obtained as a light grey solid. MS (ESI): 372.2 (MH+).

Example 3 rac-(5R,7R,8R)-8-hydroxy-7-isopropoxy-2-(4-(trifluoromethoxy)phenyl)-2-azaspiro[4.5]decan-1-one

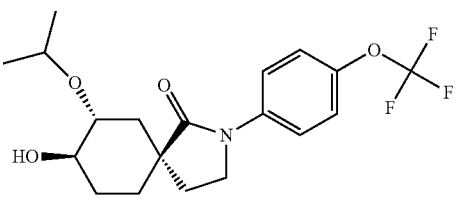 [SMILES: CC(C)O[C@@H]1C[C@@]2(CC[C@H]1O)CCN(c1ccc(OC(F)(F)F)cc1)C2=O]

Erbium(III)-trifluoromethane-sulfonate (9.4 mg) was added to a solution of the cis epoxide (1S,3R,6R)-1'-(4-(trifluoromethoxy)phenyl)-7-oxaspiro[bicyclo[4.1.0]heptane-3,3'-pyrrolidin]-2'-one (50 mg, obtained in Example 1, step 6) in 2-propanol (2.0 mL) under argon. The mixture was stirred at room temperature for 2 hours. The reaction mixture was poured into ice/water and basified with saturated NaHCO₃ solution. The aqueous phase was then extracted two times with ethyl acetate and the organic layers were washed with brine, dried over Na₂SO₄, filtered and the solvent was evaporated. The crude material was purified by two subsequent flash chromatographies (gradient of acetonitrile in dichloromethane, then gradient of ethyl acetate in heptane) to provide the title compound as a colorless solid (28 mg). MS (ESI): 388.3 (MH+).

Example 4 rac-(5R,7R,8R)-7-ethoxy-8-hydroxy-2-(4-(trifluoromethoxy)phenyl)-2-aza0spiro[4.5]decan-1-one

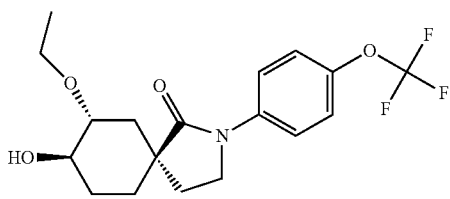 [SMILES: CCO[C@@H]1C[C@@]2(CC[C@H]1O)CCN(c1ccc(OC(F)(F)F)cc1)C2=O]

This material was obtained in analogy to Example 3 as a colorless solid (31 mg). MS (ESI): 374.2 (MH+).

Example 5 rac-(5R,7R,8R)-8-hydroxy-7-(2,2,2-trifluoroethoxy)-2-(4-(trifluoromethoxy)phenyl)-2-azaspiro[4.5]decan-1-one

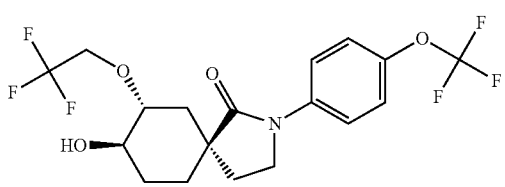 [SMILES: O=C1N(c2ccc(OC(F)(F)F)cc2)CC[C@@]12CC[C@@H](O)[C@H](OCC(F)(F)F)C2]

This material was obtained in analogy to Example 3 as a colorless solid (55 mg). MS (ESI): 428.2 (MH+).

Examples 6 and 7

(5R,7R,8R)-8-Hydroxy-7-(2,2,2-trifluoro-ethoxy)-2-(4-trifluoromethoxy-phenyl)-2-aza-spiro[4.5]decan-1-one and (5S,7S,8S)-8-hydroxy-7-(2,2,2-trifluoro-ethoxy)-2-(4-trifluoromethoxy-phenyl)-2-aza-spiro[4.5]decan-1-one

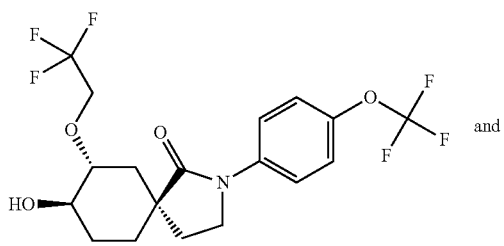

and

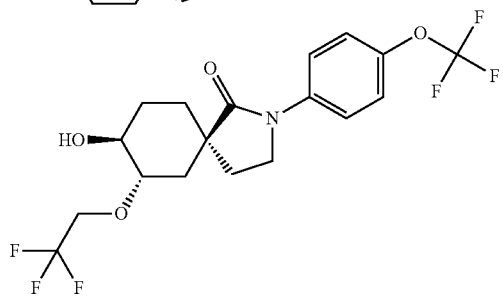

rac-(5R,7R,8R)-8-hydroxy-7-(2,2,2-trifluoroethoxy)-2-(4-(trifluoromethoxy)phenyl)-2-azaspiro[4.5]decan-1-one (25 mg, obtained in example 6) was subjected to resolution by preparative HPLC (Chiralpack AD, 30% isopropanol in heptane) to provide (5R,7R,8R)-8-hydroxy-7-(2,2,2-trifluoroethoxy)-2-(4-trifluoromethoxy-phenyl)-2-aza-spiro[4.5]decan-1-one (7 mg), MS (ESI): 428.2 (MH+),
and
(5S,7S,8S)-8-hydroxy-7-(2,2,2-trifluoro-ethoxy)-2-(4-trifluoromethoxy-phenyl)-2-aza-spiro[4.5]decan-1-one (7 mg), MS (ESI): 428.2 (MH+),
as light yellow solids.

Example 8 rac-(5R,7R,8R)-8-hydroxy-7-methoxy-2-(4-(trifluoromethoxy)phenyl)-2-azaspiro[4.5]decan-1-one

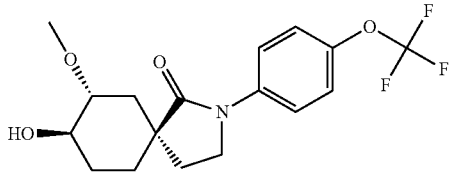 [SMILES: CO[C@@H]1C[C@@]2(CC[C@H]1O)CCN(c1ccc(OC(F)(F)F)cc1)C2=O]

This material was obtained in analogy to Example 3 as a colorless solid (74 mg). MS (ESI): 360.3 (MH$^+$).

Example 9 rac-(5R,7R,8R)-8-hydroxy-7-propoxy-2-(4-(trifluoromethoxy)phenyl)-2-azaspiro[4.5]decan-1-one

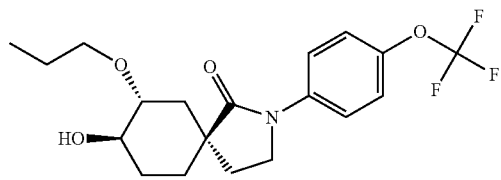 [SMILES: CCCO[C@@H]1C[C@@]2(CC[C@H]1O)CCN(c1ccc(OC(F)(F)F)cc1)C2=O]

This material was obtained in analogy to Example 3 as a colorless solid (44 mg). MS (ESI): 388.3 (MH$^+$).

Example 10 rac-(5S,7R,8R)-8-Hydroxy-7-propyl-2-[4-(2,2,2-trifluoro-ethoxy)-phenyl]-2-aza-spiro[4.5]decan-1-one

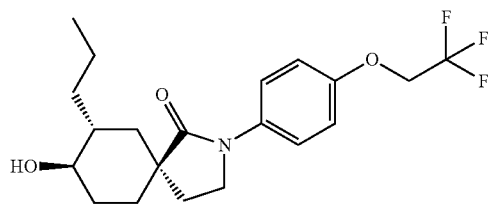 [SMILES: CCC[C@@H]1C[C@@]2(CC[C@H]1O)CCN(c1ccc(OCC(F)(F)F)cc1)C2=O]

This material was made in analogy to Example 1, Steps 1 to 7, where in reaction step 4 4-(trifluoromethoxy)-aniline was replaced with 4-(2,2,2-trifluoroethoxy)-aniline [CAS Reg. No. 57946-61-9]. Colorless solid (157 mg). MS (ESI): 386.3 (MH$^+$).

Example 11 rac-(5S,7S,8R)-8-Hydroxy-7-isopropyl-2-[4-(2,2,2-trifluoro-ethoxy)-phenyl]-2-aza-spiro[4.5]decan-1-one

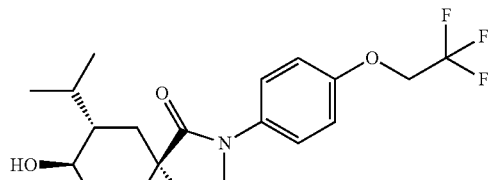

This material was obtained in analogy to Example 10 as a colorless solid (147 mg). MS (ESI): 386.2 (MH$^+$).

Example 12 rac-(5R,7R,8R)-8-Hydroxy-7-(2,2,2-trifluoro-ethoxy)-2-[4-(2,2,2-trifluoro-ethoxy)-phenyl]-2-azaspiro[4.5]decan-1-one

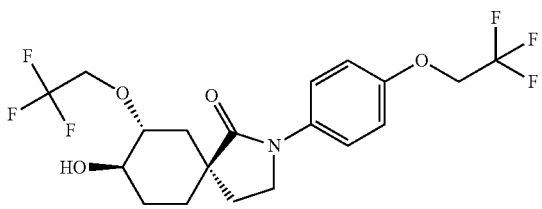 [SMILES: O=C1N(c2ccc(OCC(F)(F)F)cc2)CC[C@@]12CC[C@@H](O)[C@H](OCC(F)(F)F)C2]

This material was made in analogy to Example 1, Steps 1 to 7, where in reaction step 4 4-(trifluoromethoxy)-aniline was replaced with 4-(2,2,2-trifluoroethoxy)-aniline [CAS Reg. No. 57946-61-9]and in analogy to Example 3 for the final reaction step. The title compound was obtained as a colorless solid (56 mg). MS (ESI): 442.3 (MH$^+$).

Example 13 rac-(5R,7R,8R)-7-ethoxy-8-hydroxy-2-(4-(2,2,2-trifluoroethoxy)phenyl)-2-azaspiro[4.5]decan-1-one

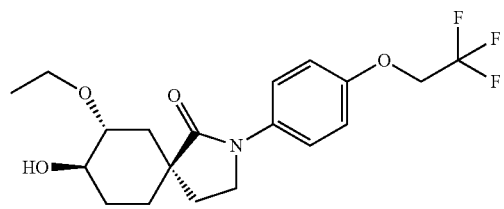 [SMILES: CCO[C@@H]1C[C@@]2(CC[C@H]1O)CCN(c1ccc(OCC(F)(F)F)cc1)C2=O]

This material was made in analogy to Example 1, Steps 1 to 7, where in reaction step 4 4-(trifluoromethoxy)-aniline was replaced with 4-(2,2,2-trifluoroethoxy)-aniline [CAS Reg. No. 57946-61-9]and in analogy to Example 3 for the final reaction step. Colorless solid (68 mg). MS (ESI): 388.3 (MH$^+$).

Example 14 rac-(5R,7R,8R)-8-hydroxy-7-isopropoxy-2-(4-(2,2,2-trifluoroethoxy)phenyl)-2-azaspiro[4.5]decan-1-one

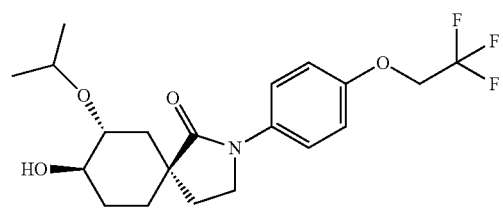 [SMILES: CC(C)O[C@@H]1C[C@@]2(CC[C@H]1O)CCN(c1ccc(OCC(F)(F)F)cc1)C2=O]

This material was made in analogy to Example 1, Steps 1 to 7, where in reaction step 4 4-(trifluoromethoxy)-aniline was replaced with 4-(2,2,2-trifluoroethoxy)-aniline [CAS Reg. No. 57946-61-9] and in analogy to Example 3 for the final reaction step. Colorless solid (67 mg). MS (ESI): 402.4 (MH⁺).

Example 15

(5R,7R,8R) and (5S,7S,8S)-8-hydroxy-7-isopropoxy-2-(4-((R)-2,2,2-trifluoro-1-methoxyethyl)phenyl)-2-azaspiro[4.5]decan-1-one

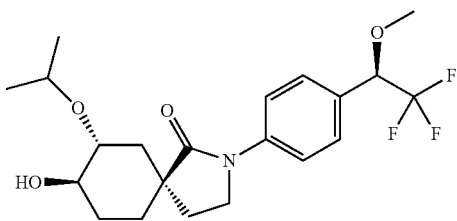 [SMILES: CO[C@H](c1ccc(N2CC[C@@]3(CC[C@@H](O)[C@H](OC(C)C)C3)C2=O)cc1)C(F)(F)F]

Step 1: 1,4-Dioxa-spiro[4.5]decane-8-carboxylic acid ethyl ester

The title compound was prepared in analogy to example 1, step 1 from ethyl-cyclohexanone-4-carboxylate [CAS Reg. No. 17159-79-4]. MS (ESI): 215.3 (MH⁺).

Step 2: 8-Cyanomethyl-1,4-dioxa-spiro[4.5]decane-8-carboxylic acid ethyl ester

A solution of 1,4-dioxa-spiro[4.5]decane-8-carboxylic acid ethyl ester (1.0 g) in THF (8 mL) was added dropwise over a period of 10 minutes to a solution of lithiumdiisopropylamide (2M in THF/heptane/ethyl benzene, 4.67 mL) in THF (12 mL) kept at −5° C. (ice/methanol bath). Stirring was continued for 1 hour at 0° C. The reaction mixture was re-cooled to −5° C. and a solution of bromoacetonitrile (0.65 mL, [CAS Reg. No. 590-17-0]) in THF (4 mL) was added dropwise over a period of 10 minutes. Stirring was then continued for 16 hours at RT. The reaction mixture was poured into ice/water and was acidified with 1M aqueous HCl solution (50 mL). The aqueous layer was extracted two times with ethyl acetate and the combined organic layers were washed with brine, dried over Na₂SO₄ and filtered. The solvent was evaporated and the residue was purified by flash chromatography (silica gel, gradient of ethyl acetate in heptane) to give the title compound as a brown liquid (528 mg, 45%). MS (ESI): 254.2 (MH⁺).

Step 3: 1,4-Dioxa-10-aza-dispiro[4.2.4.2]tetradecan-9-one

8-Cyanomethyl-1,4-dioxa-spiro[4.5]decane-8-carboxylic acid ethyl ester (525 mg) was dissolved in methanol (10 mL) and acetic acid (5 mL). Platinium(IV) oxide (235 mg) was added and an atmosphere of hydrogen was introduced. The mixture was then stirred at RT for 18 hours. The reaction was filtered over dicalite speed plus (Acros Organics) and the filtrate was concentrated in vacuo. The residue was poured into ice/water and was basified with 2M aqueous NaOH solution. The aqueous layer was extracted two times with ethyl acetate. The combined organic layers were washed with brine, dried over Na₂SO₄, filtered and the solvent was evaporated. The residue was purified by flash chromatography (silica gel, gradient of ethyl acetate in heptane) to give the title compound as a colorless solid (169 mg). MS (ESI): 212.2 (MH⁺.

Step 4: 10-[4-((R)-2,2,2-Trifluoro-1-hydroxy-ethyl)-phenyl]-1,4-dioxa-10-aza-dispiro[4.2.4.2]tetradecan-9-one 1,4-Dioxa-10-aza-dispiro[4.2.4.2]tetradecan-9-one (352 mg, obtained in example 133, step 3) was dissolved in DMF (22 mL) at RT. Then, (R)-2,2,2-trifluoro-1-(4-iodophenyl) ethanol (755 mg, for synthesis see: J. Org. Chem. 2009, 74, 1605-1610), N,N'-dimethylethylenediamine (sym) (294 mg), cuprous iodide (476 mg) and K₃PO₄ (1.06 g) were added to the reaction mixture. The mixture was heated to 80° C. for 4.5 hours. The reaction mixture was cooled down to 30° C. and more 2,2,2-trifluoro-1-(4-iodophenyl)ethanol (252 mg) was added. The mixture was re-heated to 80° C. for 2 hours. The reaction mixture was cooled, poured into ice/water and extracted two times with ethyl acetate. The combined organic layers were washed with brine, dried over Na₂SO₄, filtered and the solvent was evaporated. The residue was purified by flash chromatography (silica gel, gradient of ethyl acetate in heptane) to give the title compound as a colorless solid (415 mg, 62%). MS (ESI): 386.4 (MH⁺).

Step 5: 10-[4-((R)-2,2,2-Trifluoro-1-methoxy-ethyl)-phenyl]-1,4-dioxa-10-aza-dispiro[4.2.4.2]tetradecan-9-one Sodium hydride (60% dispersion in mineral oil, 311 mg) was combined with DMF (10 mL) under argon. The suspension was cooled down to 0° C. and a solution of 10-[(R)-4-(2,2,2-trifluoro-1-hydroxy-ethyl)-phenyl]-1,4-dioxa-10-aza-dispiro[4.2.4.2]tetradecan-9-one (1.50 g) in DMF (15 mL) was added dropwise over a period of 10 minutes. The mixture was stirred for 45 minutes at 0° C., then, iodomethane (663 mg) was added dropwise over a period of 10 minutes. The mixture was stirred at 0° C. for 15 minutes and then warmed up to RT for 1.5 hours. The reaction mixture was poured into ice/water and was extracted two times with ethyl acetate. The combined organic layers were washed with brine, dried over Na₂SO₄, filtered and the solvent was evaporated. The residue was once again evaporated with toluene (200 mL). The crude material was purified by flash chromatography (gradient of ethyl acetate in heptane) to give the title compound as a colorless solid (1.42 g). MS (ESI): 400.2 (MH⁺).

Step 6: 2-(4-((R)-2,2,2-trifluoro-1-methoxyethyl) phenyl)-2-azaspiro[4.5]decane-1,8-dione 10-[4-((R)-2,2,2-Trifluoro-1-methoxy-ethyl)-phenyl]-1, 4-dioxa-10-aza-dispiro[4.2.4.2]tetradecan-9-one (1.41 g) was dissolved in tetrahydrofuran (35.0 mL). Then hydrochloric acid (2M, 21.2 mL) was added dropwise over a period of 15 minutes to the reaction mixture. The mixture was stirred for 4.5 hours at RT and was then poured into ice/water and basified with saturated Na₂CO₃ solution. The aqueous phase was then extracted two times with ethyl acetate and the organic layers were washed brine, dried over Na₂SO₄, filtered and the solvent was evaporated. The crude material was purified by flash chromatography (gradient of ethyl acetate in heptane) to provide the title compound as a colorless solid (1.25 g). MS (ESI): 356.1 (MH$^+$).

Step 7: 8-Hydroxy-2-[4-((R)-2,2,2-trifluoro-1-methoxy-ethyl)-phenyl]-2-aza-spiro[4.5]decan-1-one 2-(4-((R)-2,2,2-trifluoro-1-methoxyethyl)phenyl)-2-azaspiro[4.5]decane-1,8-dione (1.15 g) was dissolved in methanol (30 mL) under argon. The mixture was cooled to 0° C. and sodium borohydride (184 mg) was added in three portions to the cold reaction mixture. The mixture was allowed to warm to RT for 2 hours. The reaction mixture was poured into ice/water and was extracted two times with ethyl acetate. The combined organic layers were washed with brine, dried over Na$_2$SO$_4$, filtered and the solvent was evaporated. The residue was dried at high vacuum and was used without further purification. Colorless foam (1.2 g), mixture of cis and trans alcohols. MS (ESI): 358.2 (MH$^+$).

Step 8: 2-[4-((R)-2,2,2-Trifluoro-1-methoxy-ethyl)-phenyl]-2-aza-spiro[4.5]dec-7-en-1-one This step was performed in analogy to Example 1, Step 6 to give the title compound 2-[4-((R)-2,2,2-trifluoro-1-methoxyethyl)-phenyl]-2-aza-spiro[4.5]dec-7-en-1-one as a colorless solid (1.0 g). MS (ESI): 340.1 (MH$^+$).

Step 9: (1S,3R,6R) and (1R,3S,6S)-1'-(4-((R)-2,2,2-trifluoro-1-methoxyethyl)phenyl)-7-oxaspiro[bicyclo[4.1.0]heptane-3,3'-pyrrolidin]-2'-one This step was performed in analogy to Example 1, Step 7 to give the title compound (1S,3R,6R) and (1R,3S,6S)-1'-(4-((R)-2,2,2-trifluoro-1-methoxyethyl)phenyl)-7-oxaspiro[bicyclo[4.1.0]heptane-3,3'-pyrrolidin]-2'-one as a colorless solid (1.0 g). MS (ESI): 356.1 (MH$^+$).

Step 10: (5R,7R,8R) and (5S,7S,8S)-8-hydroxy-7-isopropoxy-2-(4-((R)-2,2,2-trifluoro-1-methoxy-ethyl)phenyl)-2-azaspiro[4.5]decan-1-one This step was performed in analogy to Example 3 to provide the title compound as a colorless solid (94 mg). MS (ESI): 416.4 (MH$^+$).

Example 16

(5R,7R,8R) and (5S,7S,8S)-8-hydroxy-7-(2,2,2-trifluoroethoxy)-2-(4-((R)-2,2,2-trifluoro-1-methoxy-ethyl)phenyl)-2-azaspiro[4.5]decan-1-one

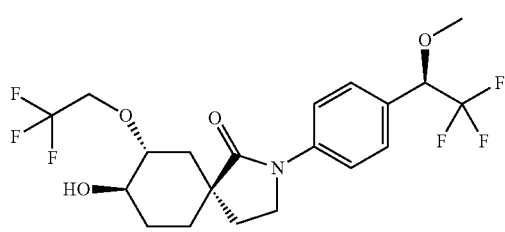 [SMILES: CO[C@H](c1ccc(N2CC[C@@]3(CC[C@@H](O)[C@H](OCC(F)(F)F)C3)C2=O)cc1)C(F)(F)F]

This material was obtained in analogy to Example 15, step 10 as a colorless foam (82 mg). MS (ESI): 456.3 (MH$^+$).

Example 17

(5R,7R,8R) and (5S,7S,8S)-2-(4-((R)-1-(benzyloxy)-2,2,2-trifluoroethyl)phenyl)-8-hydroxy-7-(2,2,2-trifluoroethoxy)-2-azaspiro[4.5]decan-1-one

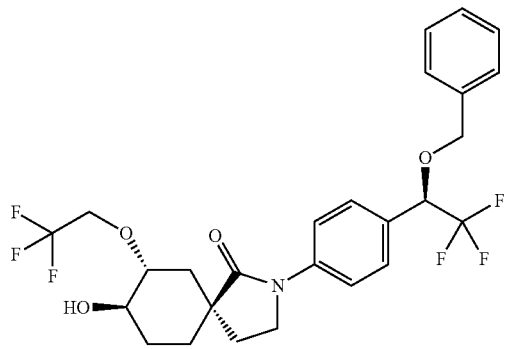 [SMILES: O=C1N(c2ccc([C@@H](OCc3ccccc3)C(F)(F)F)cc2)CC[C@@]12CC[C@@H](O)[C@H](OCC(F)(F)F)C2]

This material was made in analogy to example 15, steps 1 to 9 where in reaction step 5 iodomethane was replaced with benzylbromide in order to perform a benzylation rather than a methylation. Following that sequence, the title compound was obtained as a colorless foam (185 mg). MS (ESI): 532.1 (MH$^+$).

Example 18

(5R,7R,8R) and (5S,7S,8S)-8-hydroxy-7-(2,2,2-trifluoroethoxy)-2-(4-((R)-2,2,2-trifluoro-1-hydroxy-ethyl)phenyl)-2-azaspiro[4.5]decan-1-one

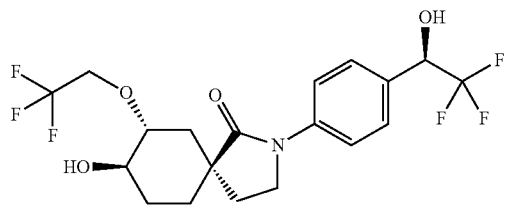 [SMILES: O=C1N(c2ccc([C@@H](O)C(F)(F)F)cc2)CC[C@@]12CC[C@@H](O)[C@H](OCC(F)(F)F)C2]

(5R,7R,8R) and (5S,7S,8S)-2-(4-((R)-1-(benzyloxy)-2,2,2-trifluoroethyl)phenyl)-8-hydroxy-7-(2,2,2-trifluoroethoxy)-2-azaspiro[4.5]decan-1-one (174 mg, from Example 17) was dissolved in methanol (12 mL). Palladium on activated charcoal (10% Pd, 52 mg) was added and the mixture was purged with hydrogen (4 times). The reaction mixture was stirred under hydrogen at RT for 3 hours. The catalyst was removed by filtration over a filter aid (dicalite, Acros Organics), washed with additional ethyl acetate and the filtrate was evaporated. The crude material was purified by flash chromatography (gradient of ethyl acetate in heptane) to provide the title compound as a colorless foam (144 mg). MS (ESI): 442.3 (MH$^+$).

Example A

A compound of formula (I) can be used in a manner known per se as the active ingredient for the production of tablets of the following composition:

|  | Per tablet |
|---|---|
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

Example B

A compound of formula (I) can be used in a manner known per se as the active ingredient for the production of capsules of the following composition:

|  | Per capsule |
|---|---|
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

The invention claimed is:

1. A compound according to formula (I),

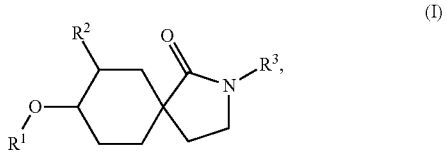

wherein
$R^1$ is selected from the group consisting of hydrogen, alkyl and cycloalkyl;
$R^2$ is selected from the group consisting of alkyl, alkoxy and haloalkoxy; and
$R^3$ is selected from the group consisting of phenyl
substituted with one to three substituents independently selected from the group consisting of haloalkoxy, hydroxyhaloalkyl, alkoxyhaloalkyl and benzyloxyhaloalkyl;
or a pharmaceutically acceptable salt thereof.

2. A compound according to claim 1, wherein $R^2$ is selected from the group consisting of methyl, ethyl, n-propyl, isopropyl, methoxy, ethoxy, n-propoxy, isopropoxy, trifluoromethoxy and trifluoroethoxy.

3. A compound according to claim 1, wherein $R^2$ is selected from the group consisting of methyl, ethyl, n-propyl, isopropyl, methoxy, ethoxy, n-propoxy, isopropoxy and trifluoroethoxy.

4. A compound according to claim 1, wherein $R^2$ is alkyl or haloalkoxy.

5. A compound according to claim 1, wherein $R^2$ is selected from the group consisting of methyl, ethyl, n-propyl, isopropyl and trifluoroethoxy.

6. A compound according to claim 1, wherein $R^2$ is alkyl.

7. A compound according to claim 1, wherein $R^2$ is selected from the group consisting of methyl, ethyl, n-propyl and isopropyl.

8. A compound according to claim 1, wherein $R^2$ is isopropyl.

9. A compound according to claim 1, wherein $R^2$ is haloalkoxy.

10. A compound according to claim 1, wherein $R^2$ is trifluoroethoxy.

11. A compound according to claim 1, wherein $R^3$ is phenyl substituted with one to three substituents independently selected from the group consisting of trifluoromethoxy, trifluoroethoxy, 2,2,2-trifluoro-1-hydroxyethyl, 2,2,2-trifluoro-1-methoxyethyl and 1-benzyloxy-2,2,2-trifluoroethyl.

12. A compound according to claim 1, wherein $R^3$ is phenyl substituted with one to three substituents independently selected from haloalkoxy and alkoxyhaloalkyl.

13. A compound according to claim 1, wherein $R^3$ is phenyl substituted with one substituent selected from the group consisting of trifluoromethoxy, trifluoroethoxy and 2,2,2-trifluoro-1-methoxyethyl.

14. A compound according to claim 1, wherein $R^3$ is phenyl substituted with one haloalkoxy substituent.

15. A compound according to claim 1, wherein $R^3$ is 4-trifluoromethoxyphenyl or 4-trifluoroethoxyphenyl.

16. A compound according to claim 1, wherein $R^3$ is phenyl substituted with one alkoxyhaloalkyl substituent.

17. A compound according to claim 1, wherein $R^3$ is phenyl substituted with one 2,2,2-trifluoro-1-methoxyethyl substituent.

18. A compound according to claim 1, wherein $R^1$ is hydrogen.

19. A compound according to claim 1, wherein said compound is a compound of formula (Ia),

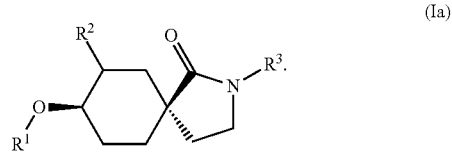

20. A compound according to claim 1, wherein said compound is a compound of formula (Ib),

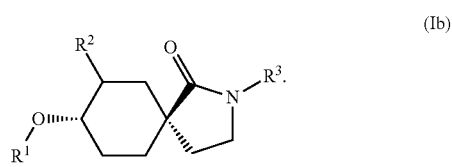

21. A compound according to claim 1, selected from the group consisting of:
rac-(5S,7R,8R)-8-hydroxy-7-propyl-2-(4-trifluoromethoxy-phenyl)-2-aza-spiro[4.5]decan-1-one;
rac-(5S,7R,8R)-8-hydroxy-7-isopropyl-2-(4-(trifluoromethoxy)phenyl)-2-azaspiro[4.5]decan-1-one;
rac-(5R,7R,8R)-8-hydroxy-7-isopropoxy-2-(4-(trifluoromethoxy)phenyl)-2-azaspiro[4.5]decan-1-one;
rac-(5R,7R,8R)-7-ethoxy-8-hydroxy-2-(4-(trifluoromethoxy)phenyl)-2-azaspiro[4.5]decan-1-one;
rac-(5R,7R,8R)-8-hydroxy-7-(2,2,2-trifluoroethoxy)-2-(4-(trifluoromethoxy)phenyl)-2-azaspiro[4.5]decan-1-one;
(5R,7R,8R)-8-hydroxy-7-(2,2,2-trifluoroethoxy)-2-(4-trifluoromethoxy-phenyl)-2-aza-spiro[4.5]decan-1-one;

(5S,7S,8S)-8-hydroxy-7-(2,2,2-trifluoroethoxy)-2-(4-trifluoromethoxy-phenyl)-2-aza-spiro[4.5]decan-1-one;
rac-(5R,7R,8R)-8-hydroxy-7-methoxy-2-(4-(trifluoromethoxy)phenyl)-2-azaspiro[4.5]decan-1-one;
rac-(5R,7R,8R)-8-hydroxy-7-propoxy-2-(4-(trifluoromethoxy)phenyl)-2-azaspiro[4.5]decan-1-one;
rac-(5S,7R,8R)-8-hydroxy-7-propyl-2-[4-(2,2,2-trifluoro-ethoxy)-phenyl]-2-aza-spiro[4.5]decan-1-one;
and pharmaceutically acceptable salts thereof.

22. A compound according to claim 1, selected from the group consisting of:
rac-(5S,7S,8R)-8-hydroxy-7-isopropyl-2-[4-(2,2,2-trifluoro-ethoxy)-phenyl]-2-aza-spiro[4.5]decan-1-one;
rac-(5R,7R,8R)-8-hydroxy-7-(2,2,2-trifluoro-ethoxy)-2-[4-(2,2,2-trifluoro-ethoxy)-phenyl]-2-aza-spiro[4.5]decan-1-one;
rac-(5R,7R,8R)-7-ethoxy-8-hydroxy-2-(4-(2,2,2-trifluoroethoxy)phenyl)-2-azaspiro[4.5]decan-1-one;
rac-(5R,7R,8R)-8-hydroxy-7-isopropoxy-2-(4-(2,2,2-trifluoroethoxy)phenyl)-2-azaspiro[4.5]decan-1-one;
(5R,7R,8R) and (5S,7S,8S)-8-hydroxy-7-isopropoxy-2-(4-((R)-2,2,2-trifluoro-1-methoxyethyl)phenyl)-2-azaspiro[4.5]decan-1-one;
(5R,7R,8R) and (5S,7S,8S)-8-hydroxy-7-(2,2,2-trifluoroethoxy)-2-(4-((R)-2,2,2-trifluoro-1-methoxyethyl)phenyl)-2-azaspiro[4.5]decan-1-one;
(5R,7R,8R) and (5S,7S,8S)-2-(4-((R)-1-(benzyloxy)-2,2,2-trifluoroethyl)phenyl)-8-hydroxy-7-(2,2,2-trifluoroethoxy)-2-azaspiro[4.5]decan-1-one;
(5R,7R,8R) and (5S,7S,8S)-8-hydroxy-7-(2,2,2-trifluoroethoxy)-2-(4-((R)-2,2,2-trifluoro-1-hydroxyethyl)phenyl)-2-azaspiro[4.5]decan-1-one;
and pharmaceutically acceptable salts thereof.

23. A compound according to claim 1, selected from the group consisting of rac-(5S,7S,8R)-8-hydroxy-7-isopropyl-2-(4-(trifluoromethoxy)phenyl)-2-azaspiro[4.5]decan-1-one;
(5S,7S,8S)-8-hydroxy-7-(2,2,2-trifluoro-ethoxy)-2-(4-trifluoromethoxy-phenyl)-2-aza-spiro[4.5]decan-1-one;
rac-(5S,7S,8R)-8-hydroxy-7-isopropyl-2-[4-(2,2,2-trifluoro-ethoxy)-phenyl]-2-aza-spiro[4.5]decan-1-one;
(5R,7R,8R) and (5S,7S,8S)-8-hydroxy-7-(2,2,2-trifluoroethoxy)-2-(4-((R)-2,2,2-trifluoro-1-methoxyethyl)phenyl)-2-azaspiro[4.5]decan-1-one;
and pharmaceutically acceptable salts thereof.

24. A pharmaceutical composition comprising a compound according to claim 1 and a therapeutically inert carrier.

* * * * *